US011364067B2

(12) United States Patent
Murrell et al.

(10) Patent No.: US 11,364,067 B2
(45) Date of Patent: Jun. 21, 2022

(54) ELECTRICAL ISOLATION OF ELECTROSURGICAL INSTRUMENTS

(71) Applicant: Ethicon LLC, Guaynabo, PR (US)

(72) Inventors: Niko Murrell, Blue Ash, OH (US); John Hibner, Mason, OH (US); Barry Worrell, Maineville, OH (US); Konstantin Zabotkin, Mason, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 869 days.

(21) Appl. No.: 15/727,121

(22) Filed: Oct. 6, 2017

(65) Prior Publication Data

US 2019/0105099 A1 Apr. 11, 2019

(51) Int. Cl.
*A61B 18/14* (2006.01)
*A61B 34/00* (2016.01)
(Continued)

(52) U.S. Cl.
CPC .......... *A61B 18/1445* (2013.01); *A61B 34/30* (2016.02); *A61B 34/37* (2016.02); *A61B 34/71* (2016.02); *A61B 34/74* (2016.02); *A61B 2017/00473* (2013.01); *A61B 2018/00077* (2013.01); *A61B 2018/00083* (2013.01); *A61B 2018/00208* (2013.01);
(Continued)

(58) Field of Classification Search
CPC ..... A61B 18/1445; A61B 18/12; A61B 18/14; A61B 2034/305; A61B 34/74; A61B 34/30; A61B 34/37; A61B 18/1206; A61B 34/71; A61B 2018/00083; A61B 2018/00208; A61B 2018/1422; A61B 2018/146; A61B 2017/00473; A61B 18/16; A61B 2018/00077; A61B 2018/00589; A61B 2018/00595; A61B 2018/00601; A61B 2018/1253; A61B 2018/126
USPC ....................................... 248/291.1
See application file for complete search history.

(56) References Cited

U.S. PATENT DOCUMENTS 6,699,177 B1* 3/2004 Wang ................. A61B 34/75
414/2
7,824,401 B2 11/2010 Manzo et al.
(Continued)

FOREIGN PATENT DOCUMENTS

WO 2010009221 A1 1/2010

OTHER PUBLICATIONS

ISRWO of corresponding PCT/IB2018/057468 dated Jul. 1, 2019.

*Primary Examiner* — Jaymi E Della
*Assistant Examiner* — Sean W Collins
(74) *Attorney, Agent, or Firm* — Vorys, Sater, Seymour and Pease LLP

(57) ABSTRACT

A surgical tool that includes a drive housing, an elongate shaft that extends from the drive housing, and an end effector arranged at a distal end of the elongate shaft and having a jaw and a jaw holder that secures the jaw. A wrist couples the end effector to the elongate shaft and includes a distal clevis having an axle that rotatably mounts the jaw holder to the distal clevis. An electrical conductor extends from the drive housing and supplies electrical energy to the jaw via a supply conductor. At least one of the jaw holder and the axle is made of a non-conductive material that insulates the distal clevis from the electrical energy provided to the jaw.

21 Claims, 22 Drawing Sheets

(51) Int. Cl.
*A61B 34/30* (2016.01)
*A61B 34/37* (2016.01)
*A61B 18/00* (2006.01)
*A61B 17/00* (2006.01)
*A61B 18/12* (2006.01)

(52) U.S. Cl.
CPC ............... *A61B 2018/00589* (2013.01); *A61B 2018/00595* (2013.01); *A61B 2018/00601* (2013.01); *A61B 2018/126* (2013.01); *A61B 2018/1253* (2013.01); *A61B 2018/146* (2013.01); *A61B 2018/1422* (2013.01); *A61B 2034/305* (2016.02)

(56) References Cited

U.S. PATENT DOCUMENTS

| | | |
|---|---|---|
| 2004/0162547 A1 | 8/2004 | Wallace |
| 2005/0240178 A1 | 10/2005 | Morley |
| 2006/0074415 A1* | 4/2006 | Scott ................. A61B 18/1445 606/45 |
| 2010/0016852 A1* | 1/2010 | Manzo ............... A61B 18/1445 606/46 |
| 2010/0016853 A1* | 1/2010 | Burbank ................ A61B 34/30 606/48 |
| 2010/0198231 A1 | 8/2010 | Scott |
| 2015/0080891 A1 | 3/2015 | Shelton, IV et al. |
| 2016/0143688 A1 | 5/2016 | Orban, III |
| 2017/0224367 A1* | 8/2017 | Kapadia ................. A61B 90/37 |
| 2018/0098780 A1* | 4/2018 | Robert ................... A61B 34/30 |

* cited by examiner

US 11,364,067 B2

ELECTRICAL ISOLATION OF ELECTROSURGICAL INSTRUMENTS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint. A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

Some surgical tools, commonly referred to as electrosurgical instruments, are electrically energized. An electrosurgical instrument has a distally mounted end effector that includes one or more electrodes. When supplied with electrical energy, the end effector electrodes are able to generate heat sufficient to cut, cauterize, and/or seal tissue.

Electrosurgical instruments can be configured for bipolar or monopolar operation. In bipolar operation, current is introduced into and returned from the tissue by active and return electrodes, respectively, of the end effector. Electrical current in bipolar operation is not required to travel long distances through the patient before returning to the return electrode. Consequently, the amount of electrical current required is minimal, which greatly reduces the risk of accidental ablations and/or burns. In addition, the two electrodes are closely spaced and within the surgeon's field of view, which further reduces the risk of unintended ablations and burns.

In monopolar operation, current is introduced into the tissue by an active (or source) end effector electrode and returned through a return electrode (e.g., a grounding pad) separately located on a patient's body. Monopolar electrosurgical instruments facilitate several surgical functions, such as cutting tissue, coagulating tissue to stop bleeding, or concurrently cutting and coagulating tissue. The surgeon can apply a current whenever the conductive portion of the instrument is in electrical proximity with the patient, permitting the surgeon to operate with monopolar electrosurgical instruments from many different angles.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

Figure 14:
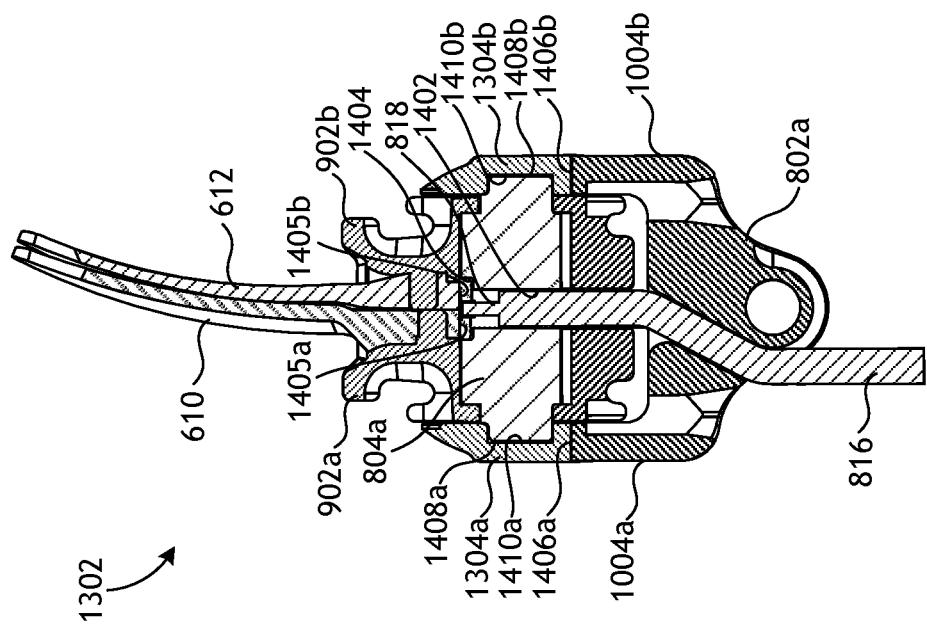
Figure 13:
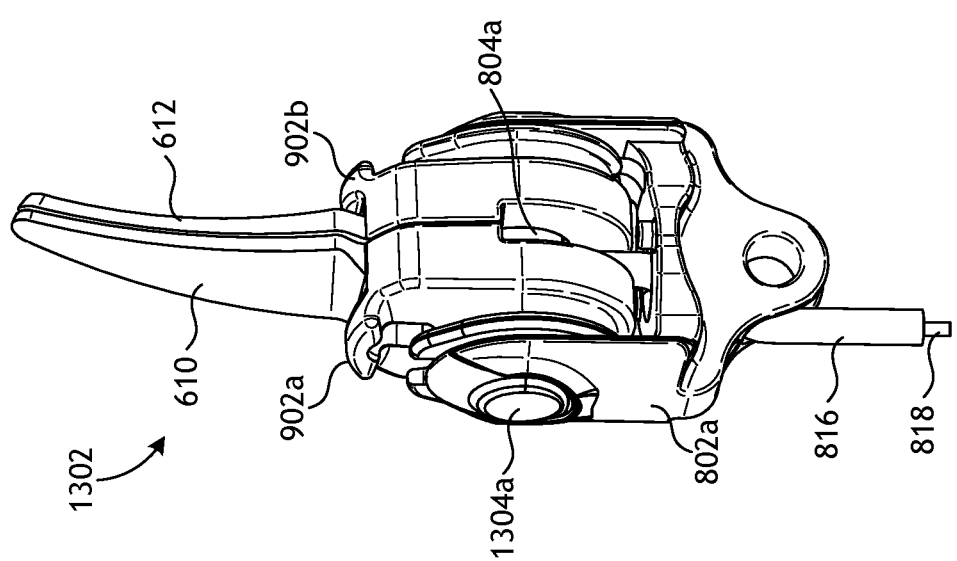
FIG. 13 is an enlarged view of another example end effector that might be used with the surgical tool of FIG. 6.

The FIG. 14 is a cross-sectional front view of the end effector of FIG. 13.

Figure 15:
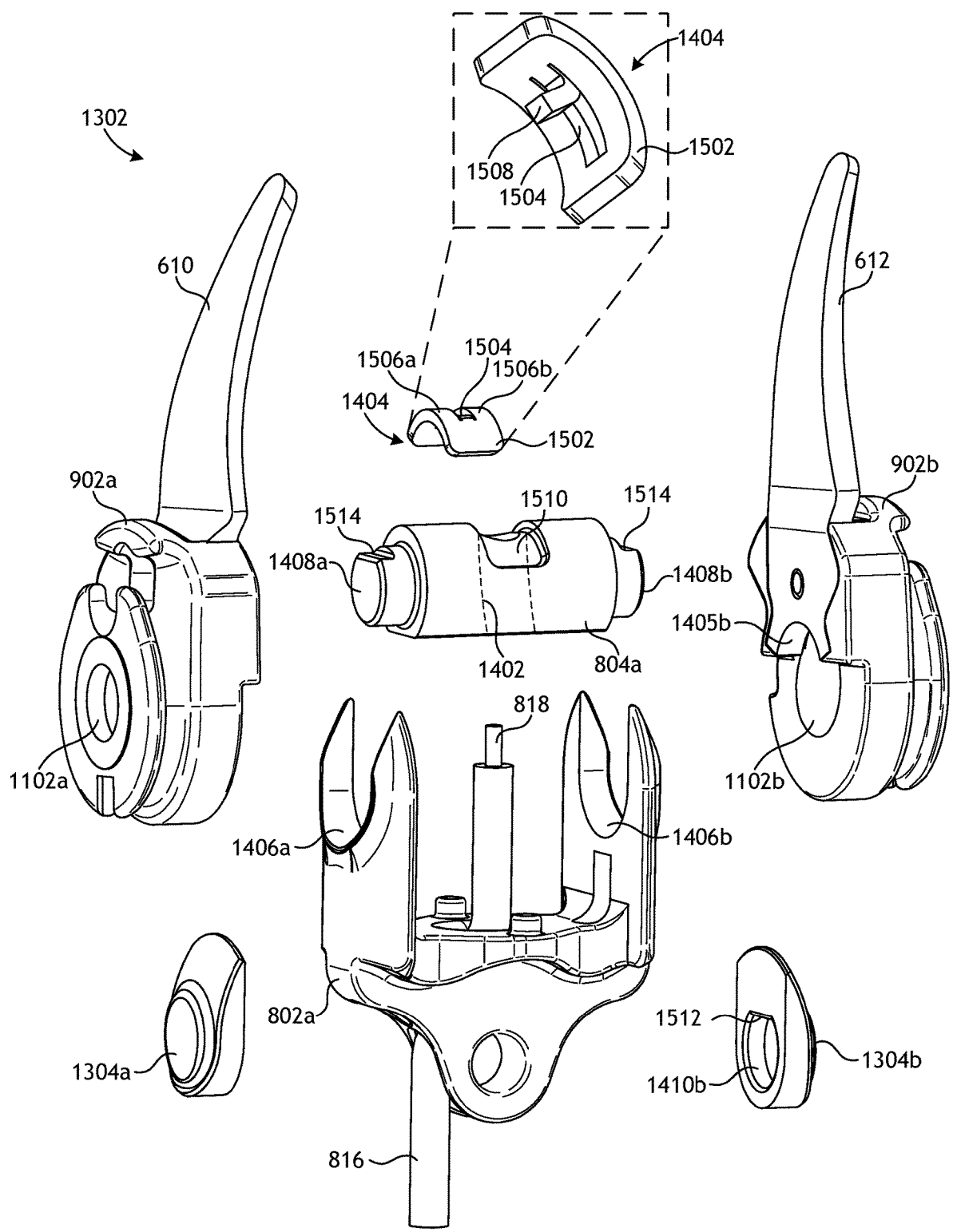

FIG. 15 is an isometric exploded view of the end effector of FIG. 13.

Figure 6:
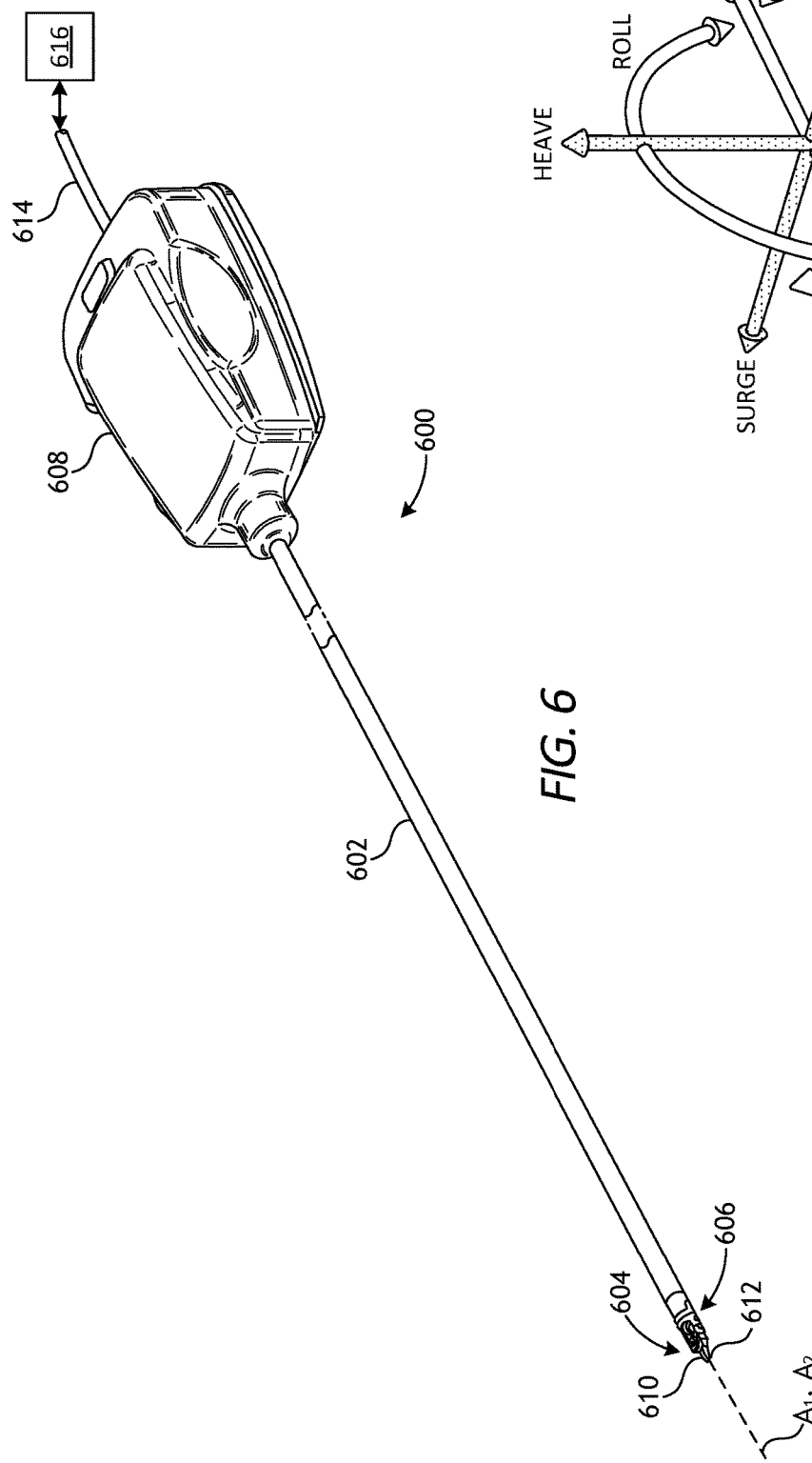
FIG. 6 is a side view of an example surgical tool that may incorporate some or all of the principles of the present disclosure.
Figure 16:
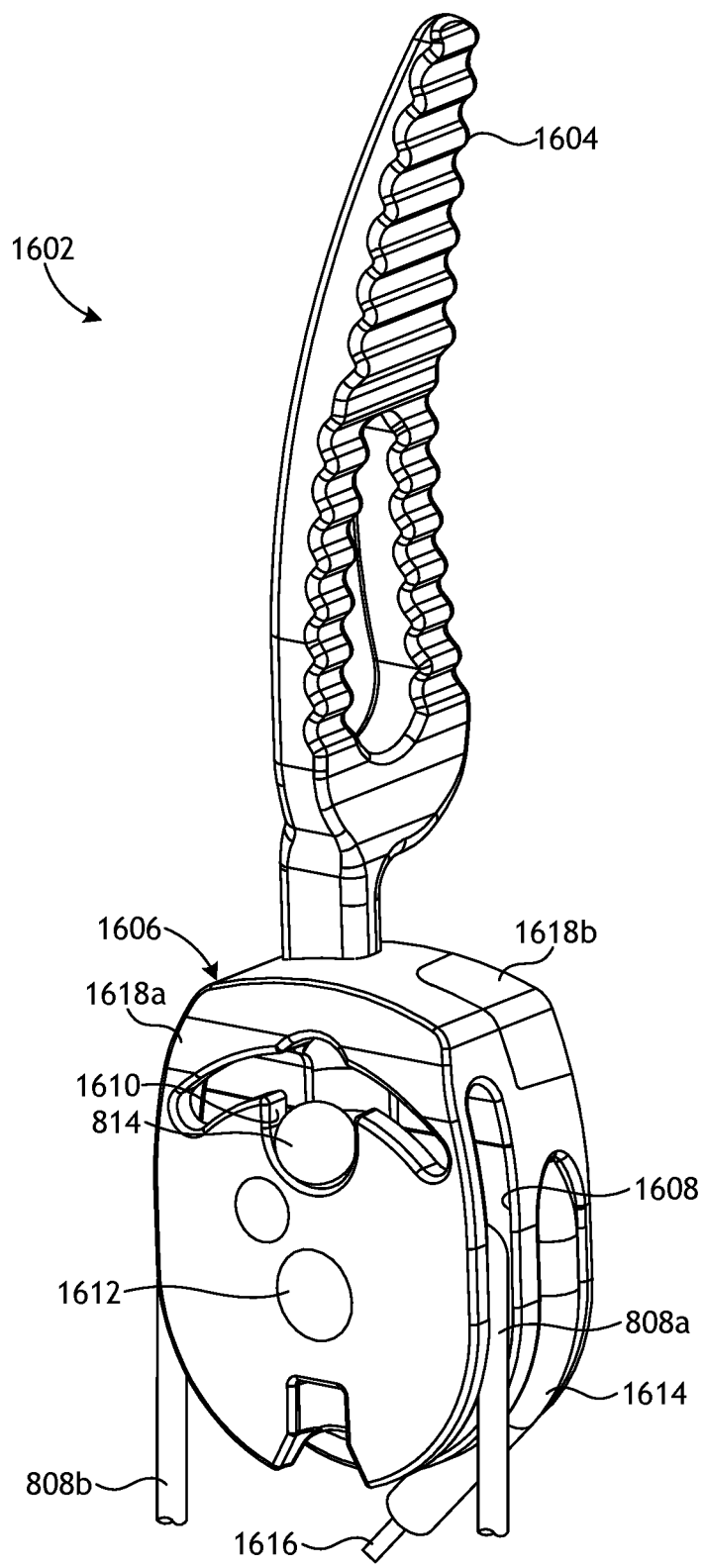

FIG. 16 is an isometric view of a portion of another example end effector that might be used with the surgical tool of FIG. 6.

Figure 17:
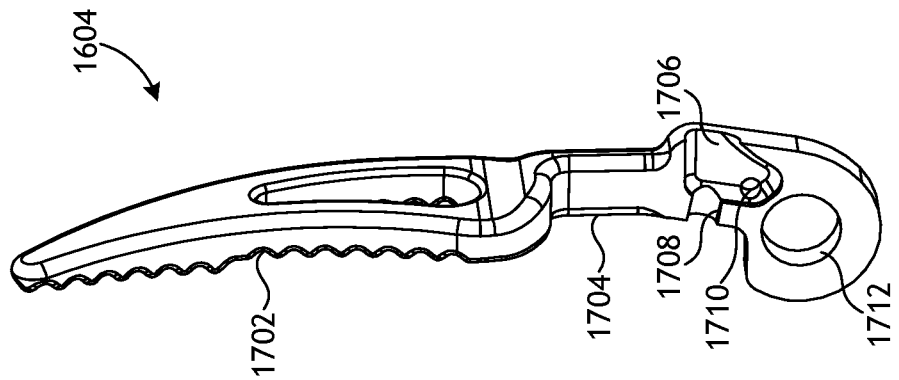

FIG. 17 is an isometric side view of the jaw of FIG. 16.

Figure 18B:
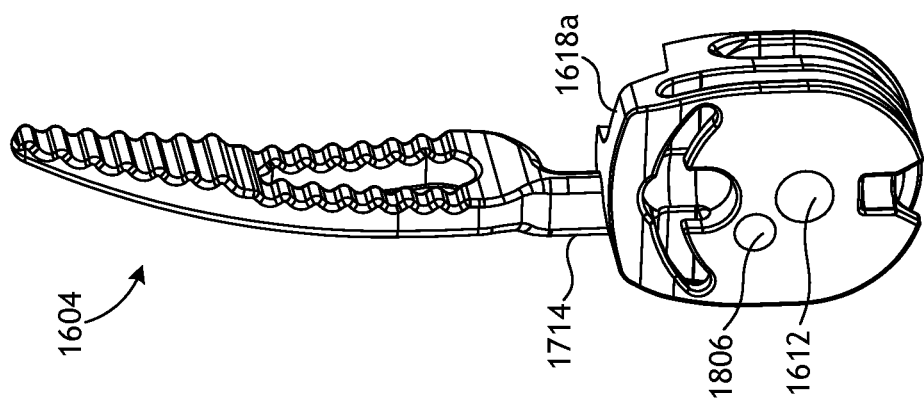
Figure 18A:
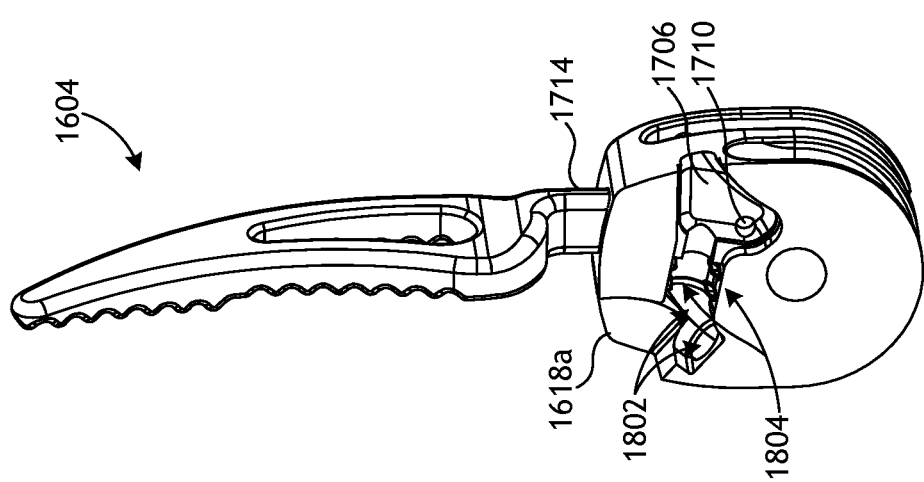

FIGS. 18A and 18B are front and back views, respectively, of the first portion of the jaw holder of FIG. 16 following a first overmold shot.

Figure 19:
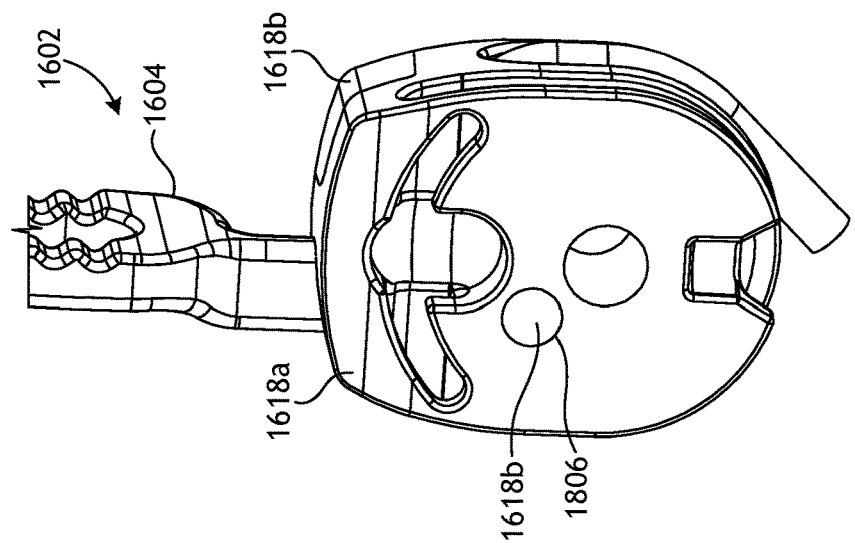

FIG. 19 depicts the electrical conductor received within the first portion of the jaw holder of FIG. 16.

Figure 20A:
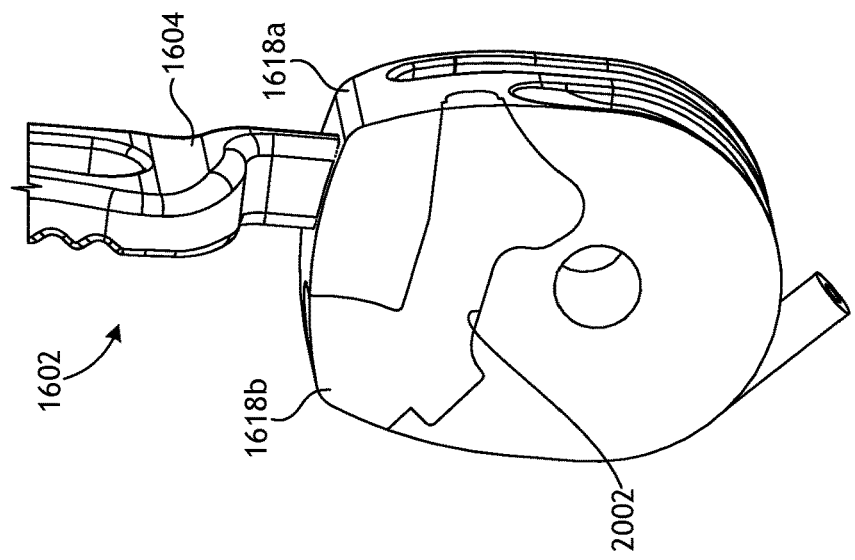
Figure 20B:
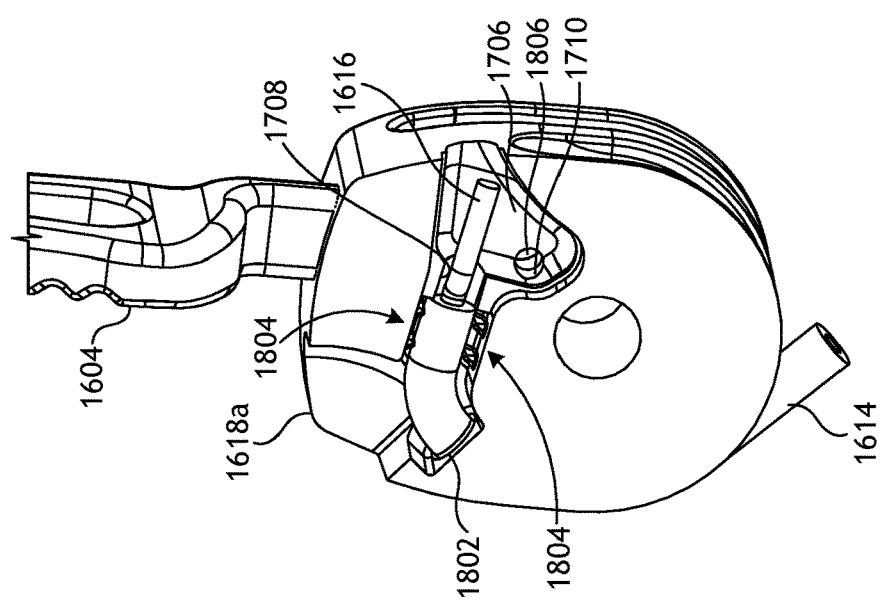

FIGS. 20A and 20B are front and back views, respectively, of the end effector of FIG. 16 following a second overmold shot.

Figure 21:
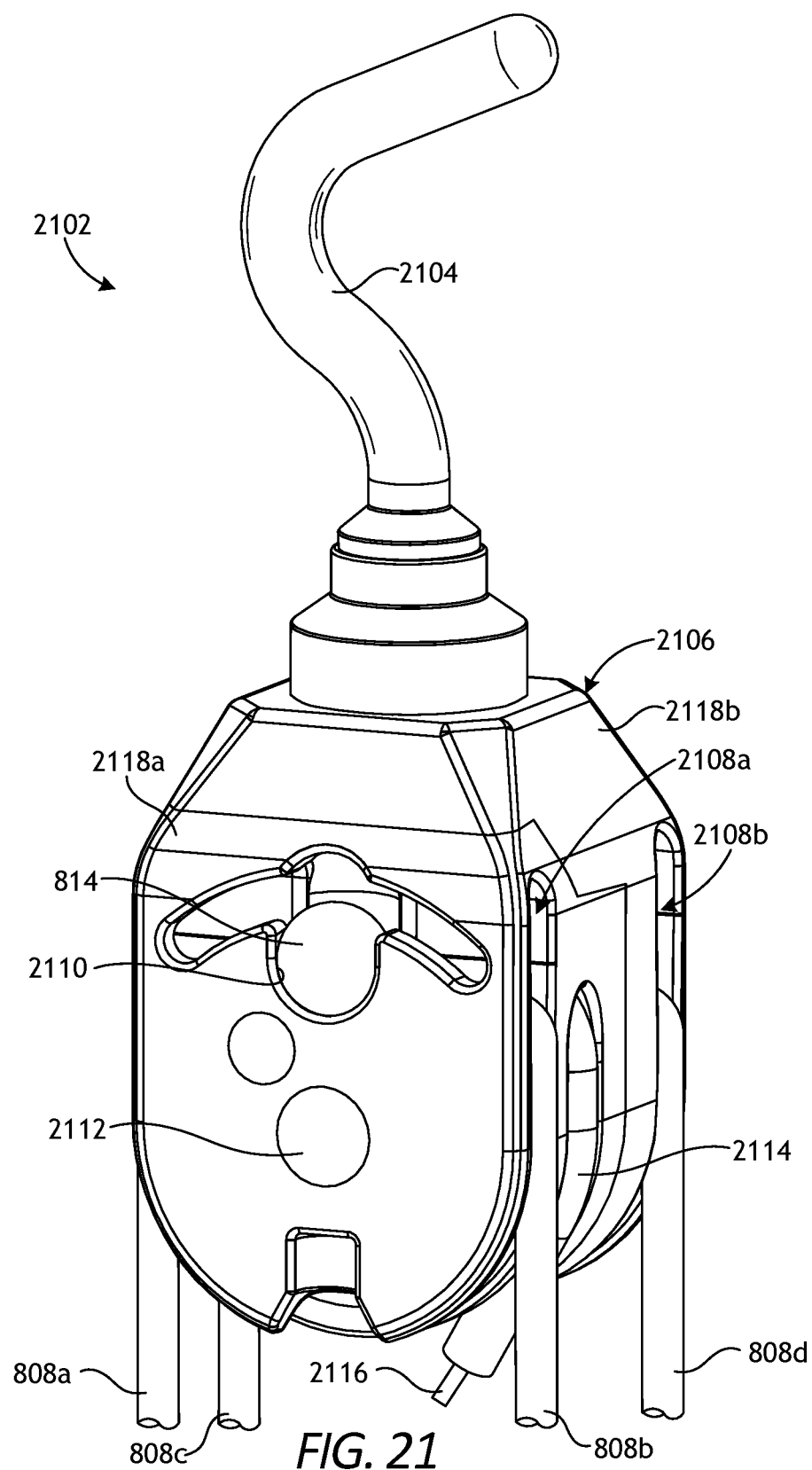

FIG. 21 is an isometric view of another example end effector, according to one or more embodiments.

Figure 22:
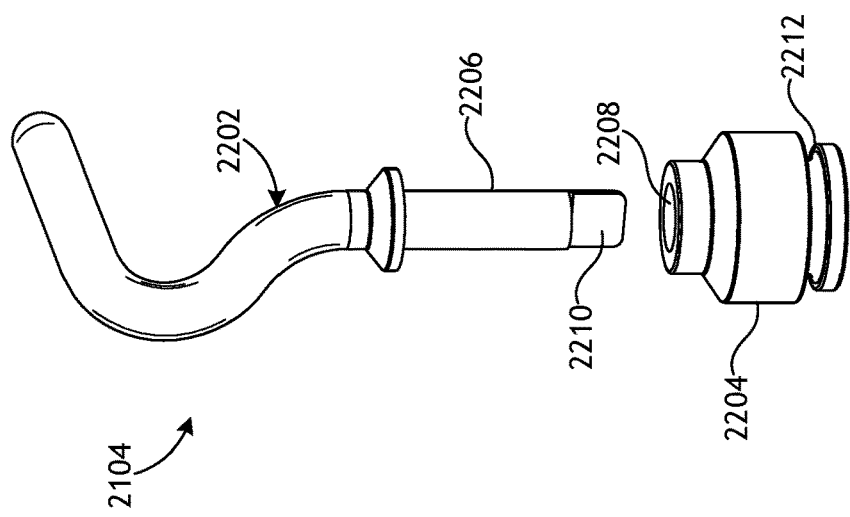

FIG. 22 is an isometric side view of the jaw of FIG. 21.

Figure 23:
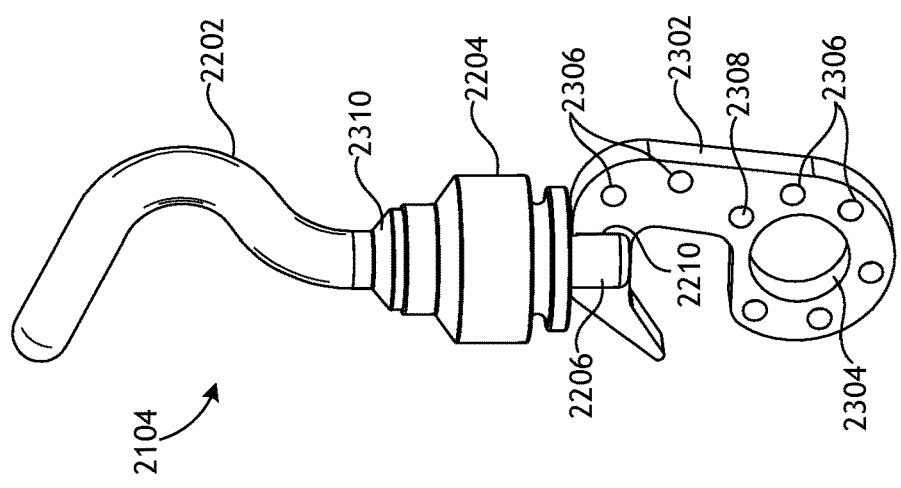

FIG. 23 is another isometric side view of the jaw of FIG. 21.

Figure 24A:
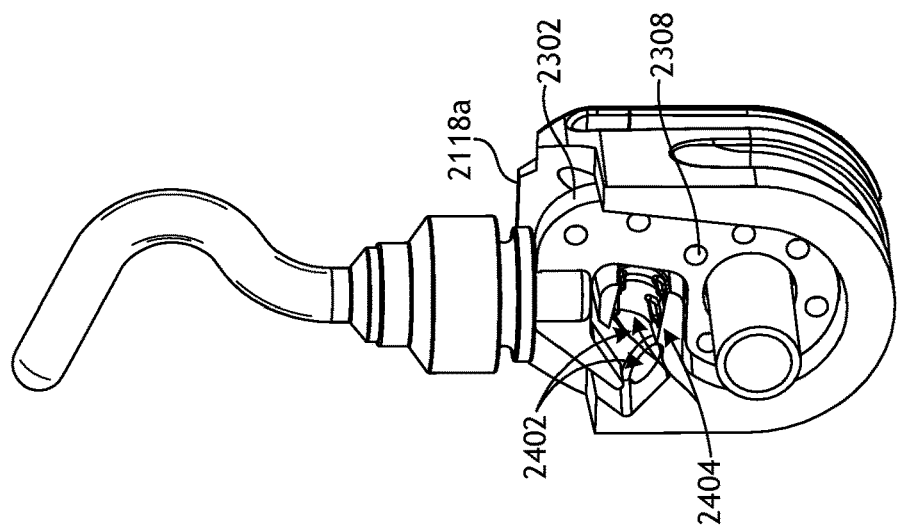
Figure 24B:
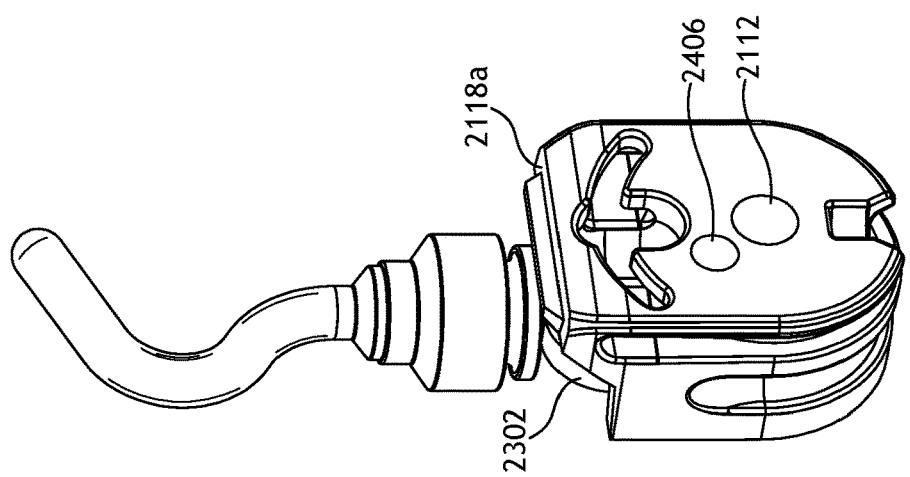

FIGS. 24A and 24B are front and back views, respectively, of the first portion of the jaw holder of FIG. 21 following a first assembly sequence.

Figure 25:
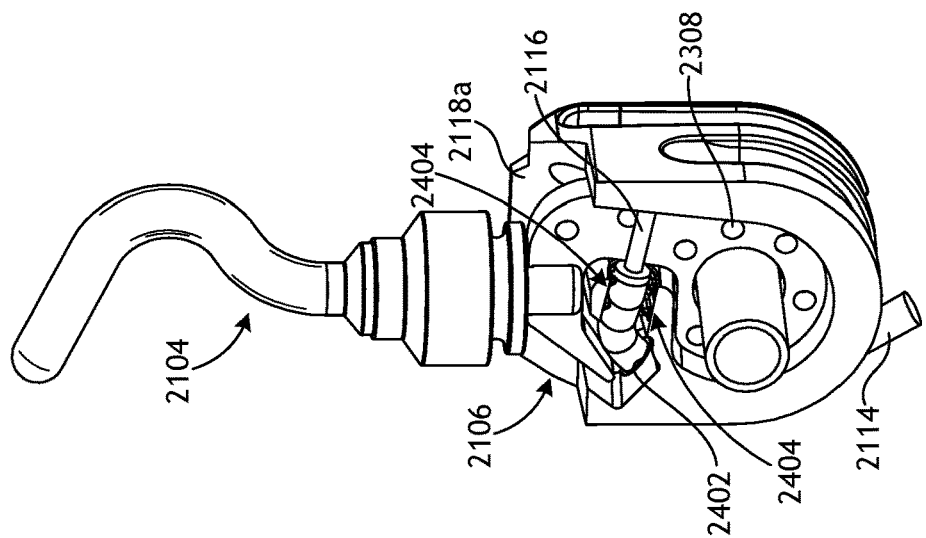

FIG. 25 depicts the electrical conductor received within the first portion of the jaw holder 2106 of FIG. 21.

Figure 26A:
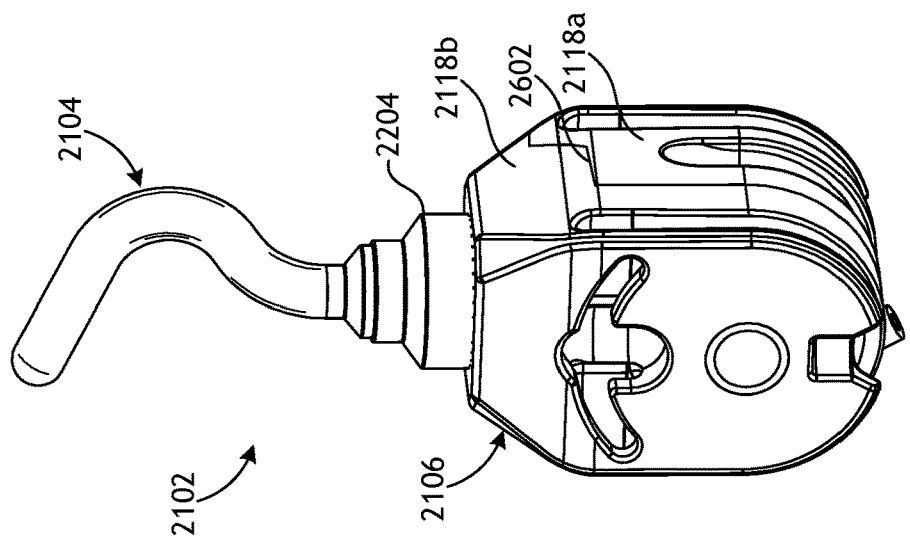
Figure 26B:
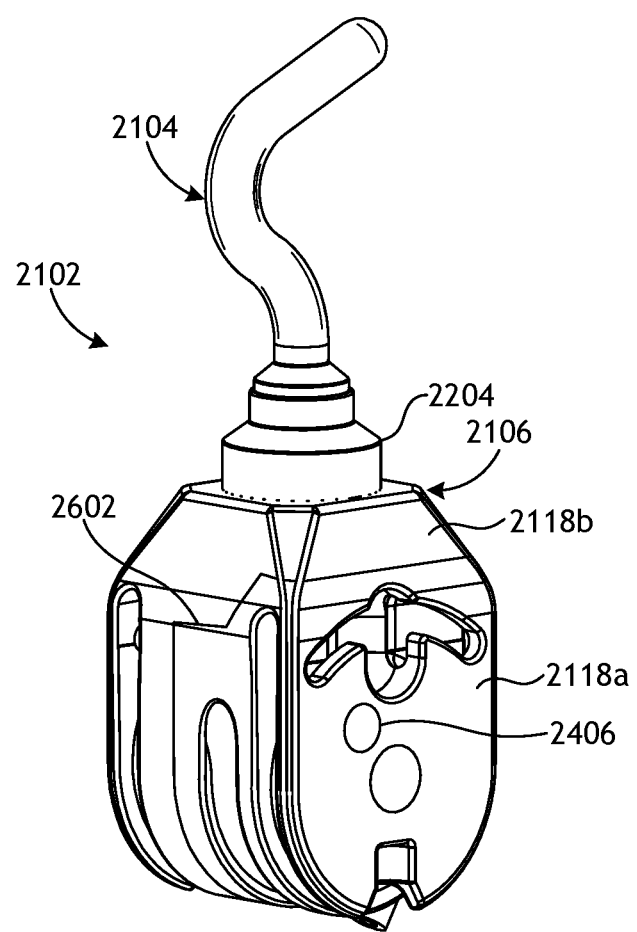

FIGS. 26A and 26B are front and back views, respectively, of the end effector of FIG. 21 following a second assembly sequence.

Figure 27:
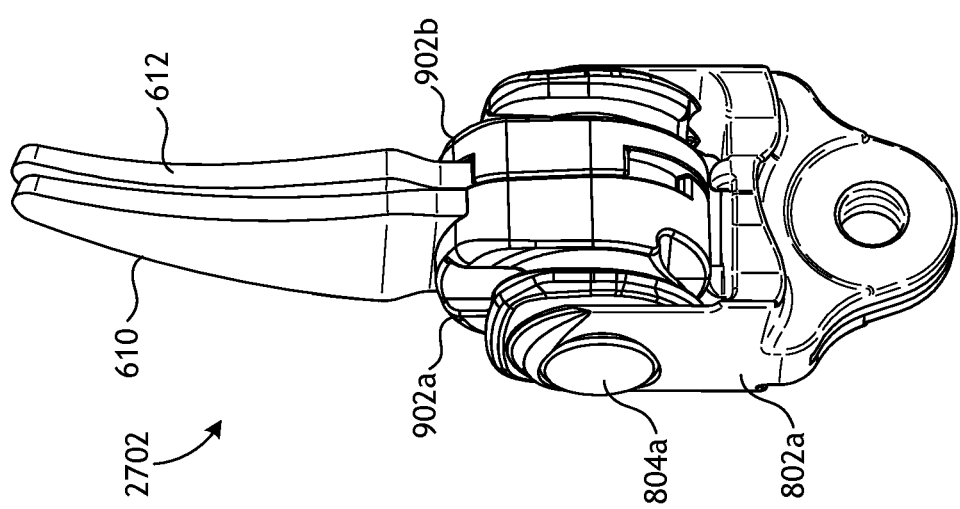

FIG. 27 is an enlarged isometric view of another example end effector that may be used with the surgical tool of FIG. 6.

Figure 28:
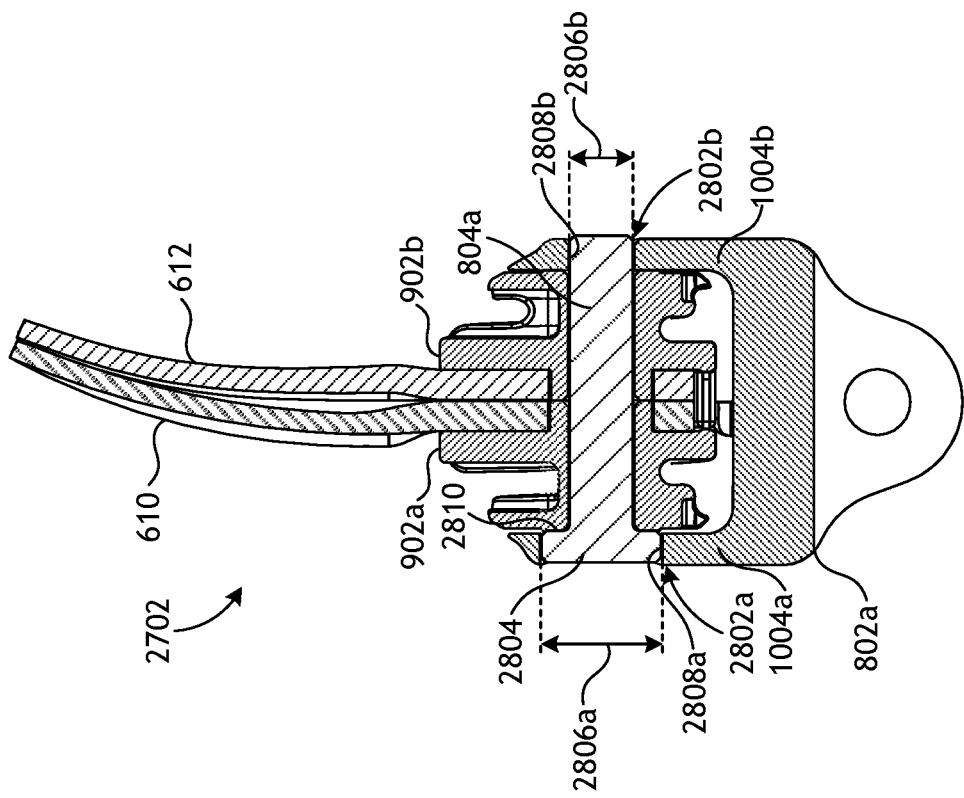

FIG. 28 is a cross-sectional front view of the end effector of FIG. 27.

Figure 29:
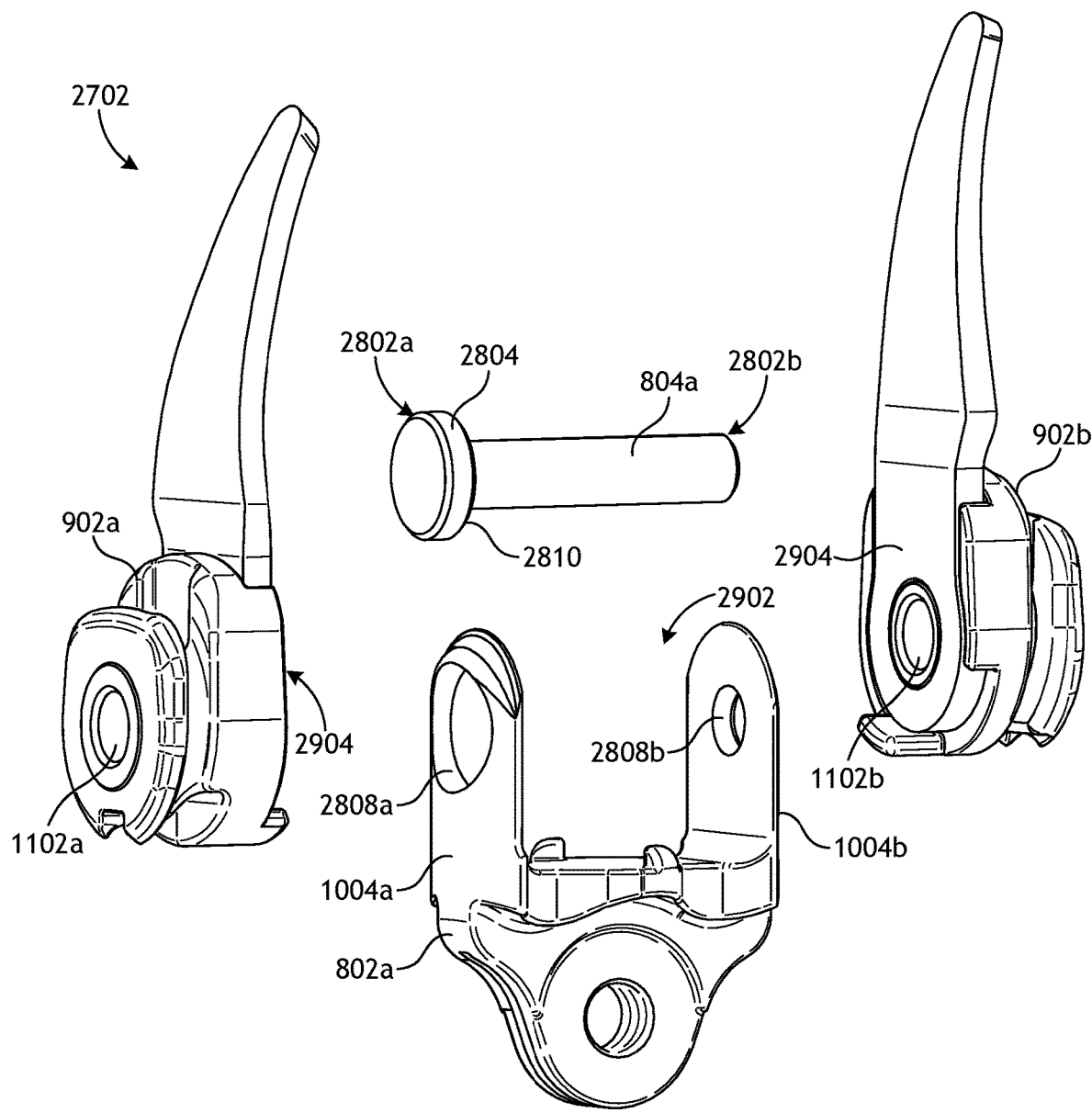

FIG. 29 is an exploded view of the end effector of FIG. 27.

DETAILED DESCRIPTION

The present disclosure is related to robotic surgical systems and, more particularly, to electrosurgical instruments having an end effector designed to insulate an electrical conductor from conductive materials that form part of the end effector.

Embodiments discussed herein describe electrosurgical instruments that use electrical energy to perform a variety of surgical procedures. End effectors that may be used with the electrosurgical instruments include a distal clevis, an axle mounted to the distal clevis, and a jaw holder rotatably mounted to the axle. A jaw may be secured to the jaw holder such that rotation of the jaw holder about the axle correspondingly rotates the jaw. An electrical conductor may supply electrical energy to the jaw via a supply conductor, and at least one of the jaw holder and the axle may be made of a non-conductive material that may prove advantageous in insulating the distal clevis from the electrical energy provided to the jaw.

Figure 1:
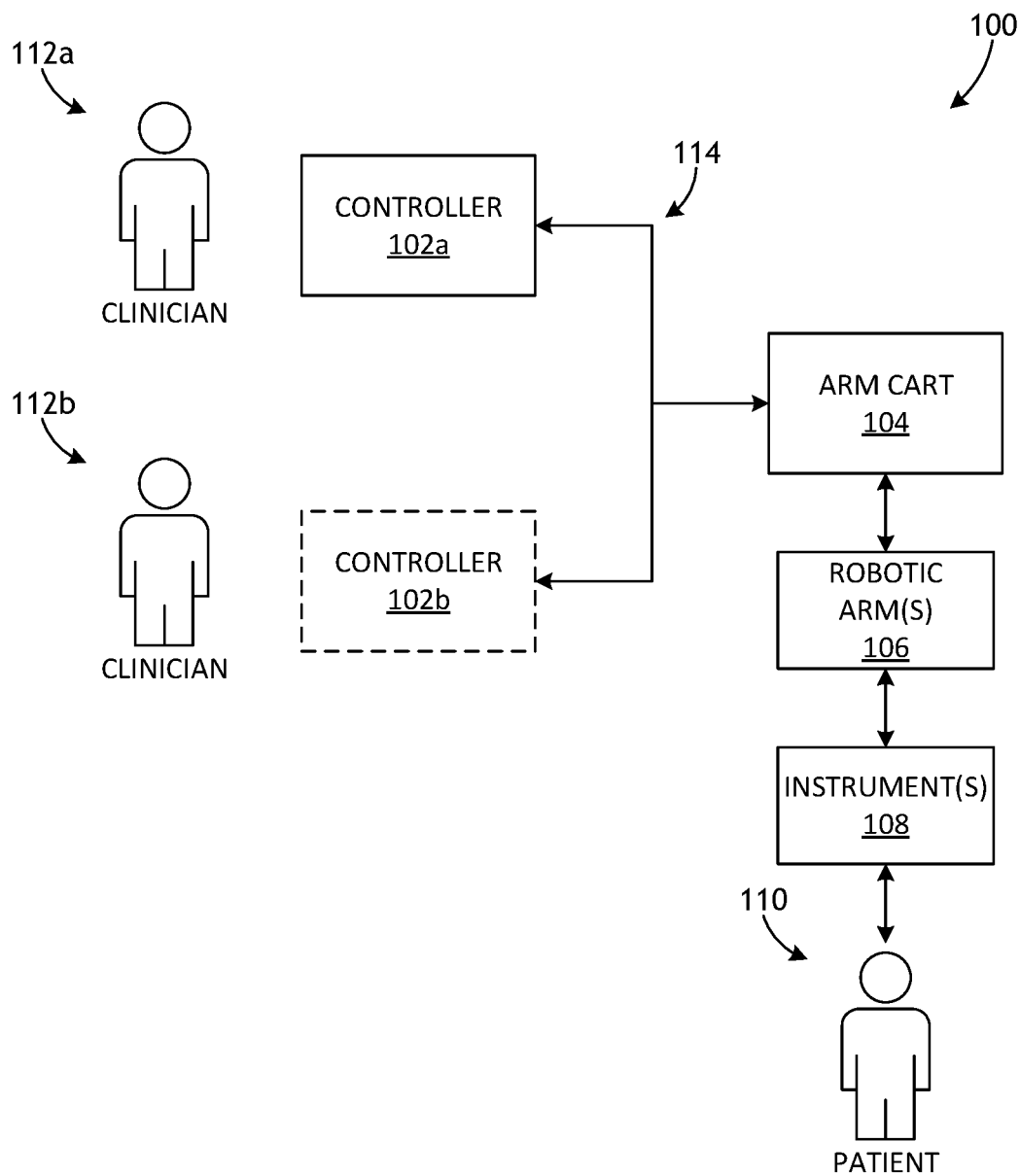
FIG. 1 is a block diagram of an example robotic surgical system that may incorporate some or all of the principles of the present disclosure.

FIGS. 1-5 illustrate the structure and operation of example robotic surgical systems and components thereof. FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient 110. Operation of the arm cart 104, including the arms 106 and instruments 108 may be directed by a clinician 112a (e.g., a surgeon) from the master controller 102a.

In some embodiments, a second master controller 102b (shown in dashed lines) operated by a second clinician 112b may also direct operation of the arm cart 104 in conjunction with the first clinician 112a. In such embodiments, for example, each clinician 102a,b may control different arms 106 of the arm cart 104 or, in some cases, complete control of the arm cart 104 may be passed between the clinicians 102a,b. In some embodiments, additional arm carts (not shown) may be utilized on the patient 110, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
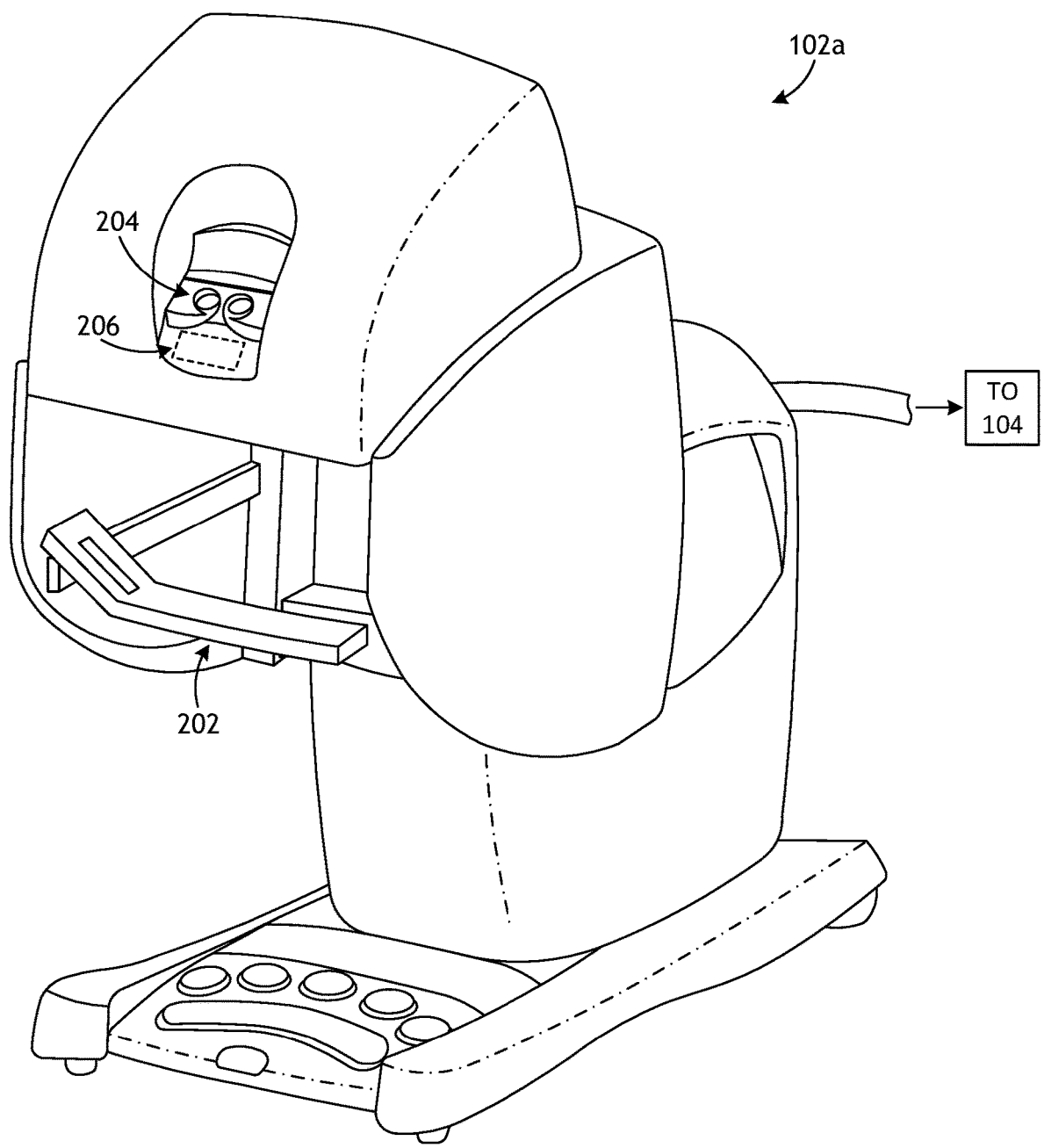
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician 112a of FIG. 1) and manipulated in space while the surgeon views the procedure via a stereo display 204. The master controllers 202 generally comprise manual input devices designed to move in multiple degrees of freedom, and which often further have an actuatable handle for actuating a surgical instrument (e.g., the surgical instrument (s) 108 of FIG. 1), for example, for opening and closing opposing jaws, applying an electrical potential (current) to an electrode, or the like.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
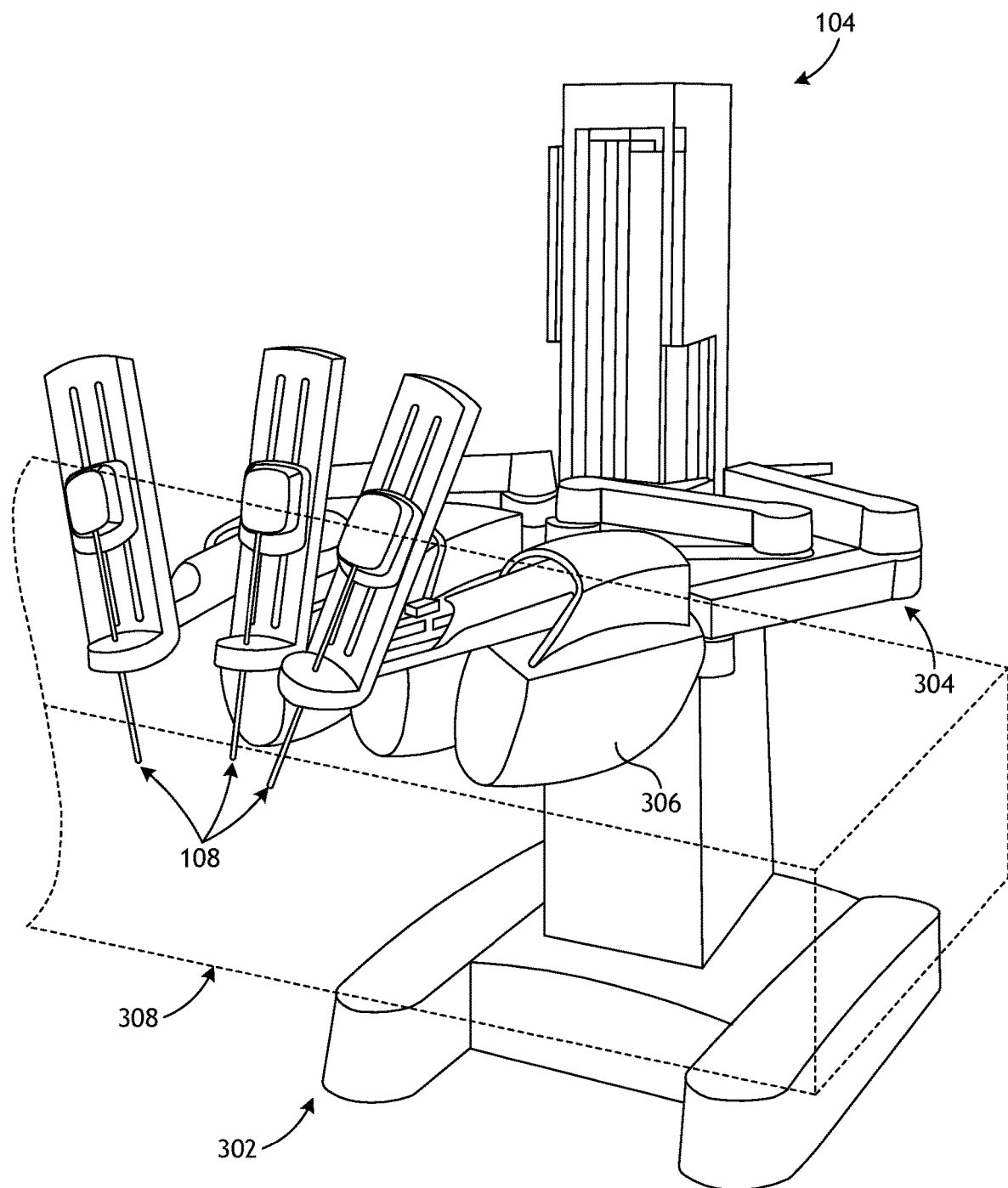
FIG. 3 depicts an example embodiment of the robotic arm cart of FIG. 1 used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of manually articulatable linkages, generally referred to as set-up joints 304, and a robotic manipulator 306. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 104.

The cart 104 will generally have dimensions suitable for transporting the cart 104 between operating rooms. The cart 104 may be configured to fit through standard operating room doors and onto standard hospital elevators. In some embodiments, the cart 104 may include a wheel system (or other transportation system) that allows the cart 104 to be positioned adjacent an operating table by a single attendant. In various embodiments, an automated reloading system including a base portion may be strategically located within a work envelope 308 of the robotic arm cart 104.

Figure 4:
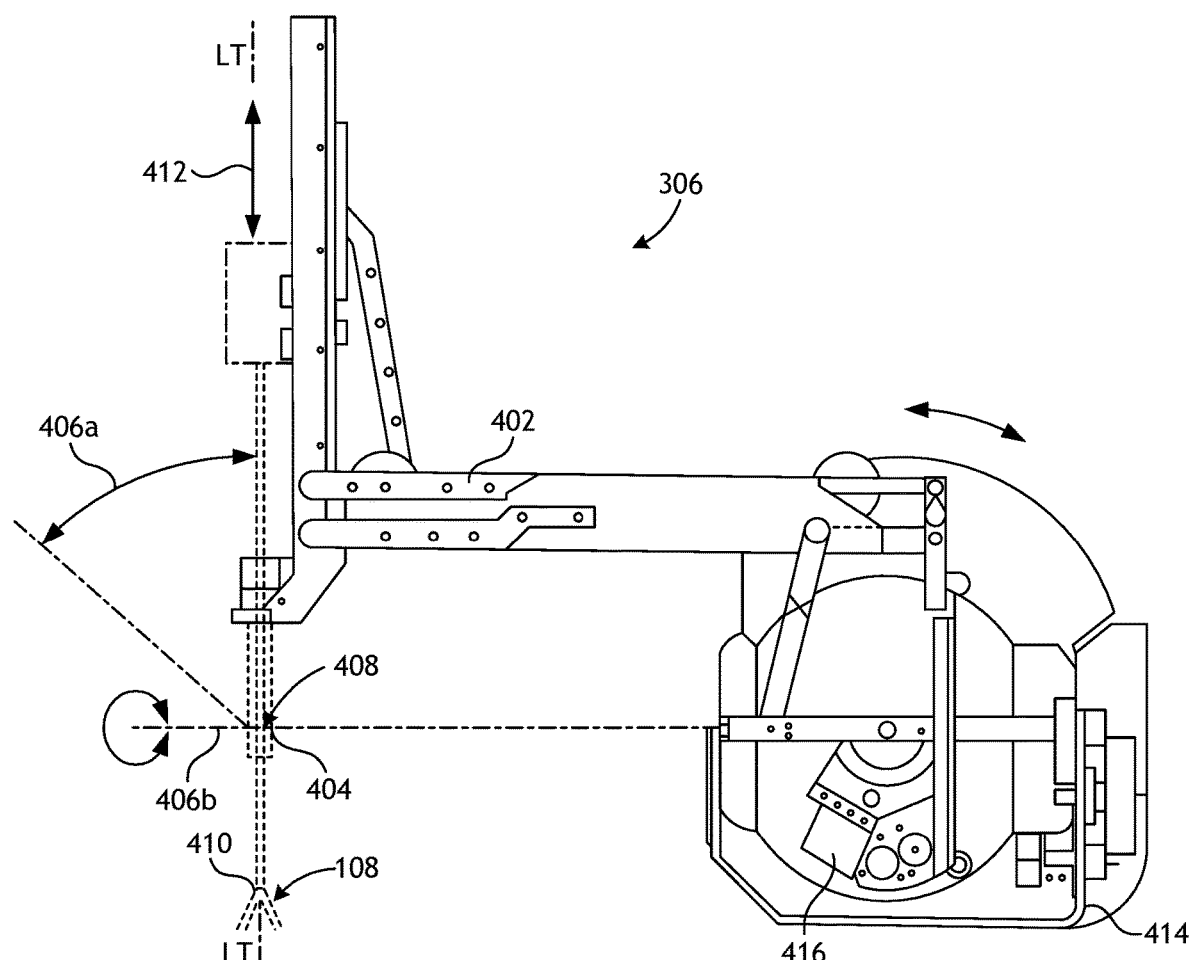
FIG. 4 is a side view schematic diagram of an example embodiment of the robotic manipulator of FIG. 3.

FIG. 4 is a side view schematic diagram of an example embodiment of the robotic manipulator 306. As illustrated, the robotic manipulator 306 may include linkage 402 that constrains movement of the surgical instrument 108 coupled thereto. The linkage 402 includes rigid links coupled by rotational joints in a parallelogram arrangement so that the surgical instrument 108 rotates around a point 404 in space.

The parallelogram arrangement constrains rotation to pivoting about a "pitch axis" that extends axis through the point 404, as indicated by a pitch arrow 406a. The links supporting the parallelogram linkage 402 are pivotally mounted to set-up joints 304 (FIG. 3) so that the surgical instrument 108 further rotates about a second axis 406b, referred to as the "yaw axis." The pitch axis and the yaw axis 406b intersect at a remote center 408, which is aligned along a shaft 410 of the surgical instrument 108.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the tool driver 306 (arrow 412), the remote center 408 remains fixed relative to a base 414 of the tool driver 306. Hence, the entire tool driver 306 is generally moved to re-position the remote center 408.

The linkage 402 of the tool driver 306 is driven by a series of motors 416. These motors 416 actively move the linkage 402 in response to commands from a processor of a control system. The motors 416 may also be employed to manipulate the surgical instrument 108.

Figure 5:
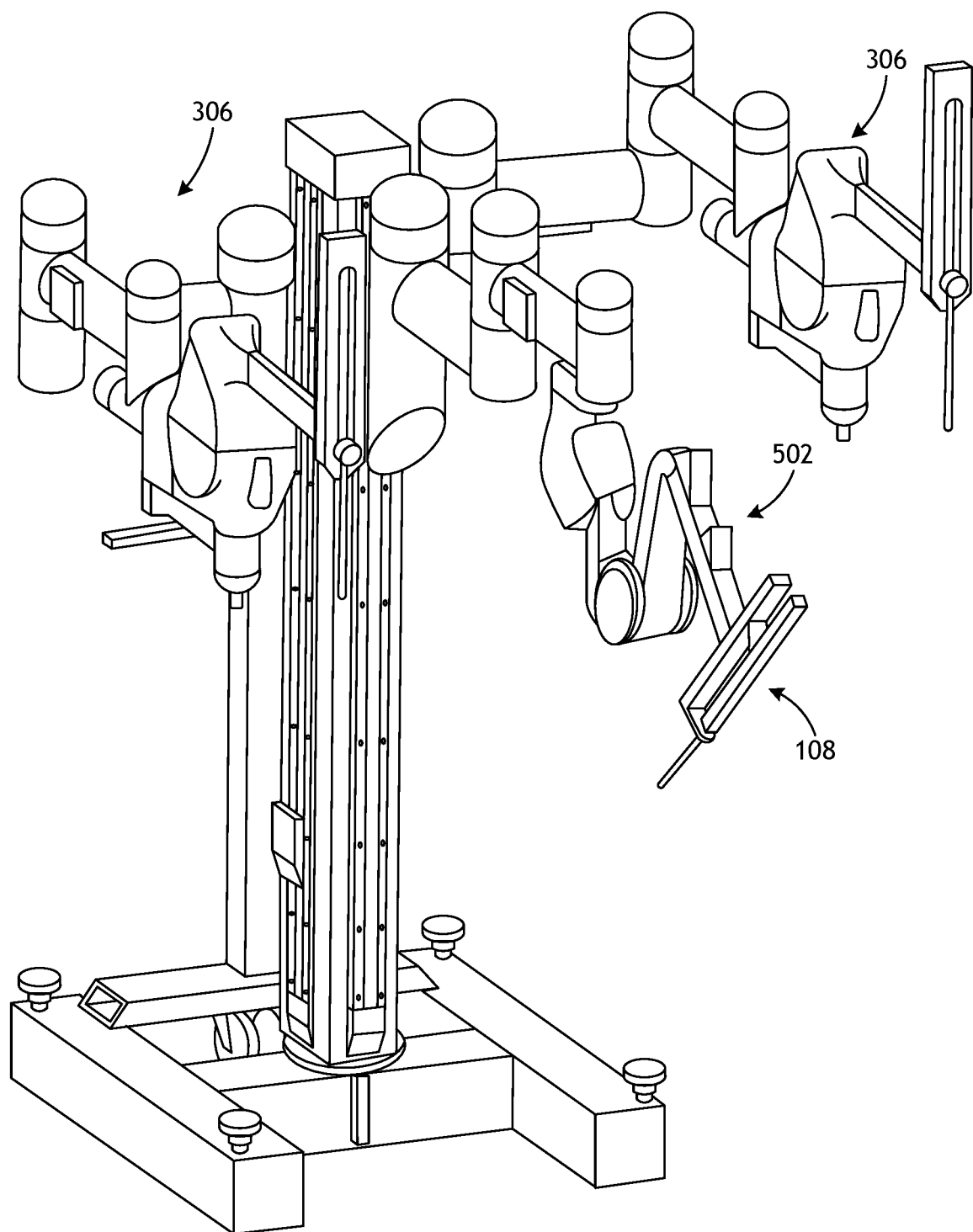
FIG. 5 is a perspective view of an alternative example robotic manipulator.

FIG. 5 is a perspective view of an alternative example robotic manipulator 502, used in conjunction with two robotic manipulators similar to the robotic manipulators 306 described in FIG. 4. As illustrated, a surgical instrument 108 is supported by the robotic manipulator 502 between the two robotic manipulators 306 generally described above. Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system is primarily described herein with reference to communication between the surgical instrument 108 and the master controller 102a (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

FIG. 6 is side view of an example surgical tool 600 that may incorporate some or all of the principles of the present disclosure. The surgical tool 600 may be the same as or similar to the surgical instrument(s) 108 of FIGS. 1 and 3-5) and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100. In other embodiments, however, the surgical tool 600 may be adapted for use in a manual or hand-operated manner, without departing from the scope of the disclosure.

As illustrated, the surgical tool 600 includes an elongate shaft 602, an end effector 604, a wrist 606 (alternately referred to as a "wrist joint") that couples the end effector 604 to the distal end of the shaft 602, and a drive housing 608 coupled to the proximal end of the shaft 602. In applications where the surgical tool is used in conjunction with a robotic surgical system (e.g., the robotic surgical system 100 of FIG. 1), the drive housing 608 can include coupling features that releasably couple the surgical tool 600 to the robotic surgical system.

The terms "proximal" and "distal" are defined herein relative to a robotic surgical system having an interface configured to mechanically and electrically couple the surgical tool 600 (e.g., the housing 608) to a robotic manipulator. The term "proximal" refers to the position of an element closer to the robotic manipulator and the term "distal" refers to the position of an element closer to the end effector 604 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 604 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 600, the end effector 604 is configured to move (pivot) relative to the shaft 602 at the wrist 606 to position the end effector 604 at desired orientations and locations relative to a surgical site. The housing 608 includes (contains) various mechanisms designed to control operation of various features associated with the end effector 604 (e.g., clamping, firing, rotation, articulation, energy delivery, etc.). In at least some embodiments, the shaft 602, and hence the end effector 604 coupled thereto, is configured to rotate about a longitudinal axis $A_1$ of the shaft 602. In such embodiments, at least one of the mechanisms included (housed) in the housing 608 is configured to control rotational movement of the shaft 602 about the longitudinal axis $A_1$.

The surgical tool 600 can have any of a variety of configurations capable of performing at least one surgical function. For example, the surgical tool 600 may include, but is not limited to, forceps, a grasper, a needle driver, scissors, an electro cautery tool, a stapler, a clip applier, a hook, a spatula, a suction tool, an irrigation tool, an imaging device (e.g., an endoscope or ultrasonic probe), or any combination thereof. In some embodiments, the surgical tool 600 may be configured to apply energy to tissue, such as radio frequency (RF) energy.

The shaft 602 is an elongate member extending distally from the housing 608 and has at least one lumen extending therethrough along its axial length. In some embodiments, the shaft 602 may be fixed to the housing 608, but could alternatively be rotatably mounted to the housing 608 to allow the shaft 602 to rotate about the longitudinal axis $A_1$.

In yet other embodiments, the shaft 602 may be releasably coupled to the housing 608, which may allow a single housing 608 to be adaptable to various shafts having different end effectors.

The end effector 604 can have a variety of sizes, shapes, and configurations. In the illustrated embodiment, the end effector 604 comprises surgical scissors that include opposing jaws 610, 612 (alternately referred to as "blades") configured to move (articulate) between open and closed positions. As will be appreciated, however, the opposing jaws 610, 612 may alternatively form part of other types of end effectors such as, but not limited to, a tissue grasper, a clip applier, a needle driver, a babcock including a pair of opposed grasping jaws, bipolar jaws (e.g., bipolar Maryland grasper, forceps, a fenestrated grasper, etc.), etc. One or both of the jaws 610, 612 may be configured to pivot at the wrist 606 to articulate the end effector 604 between the open and closed positions.

Figure 7:
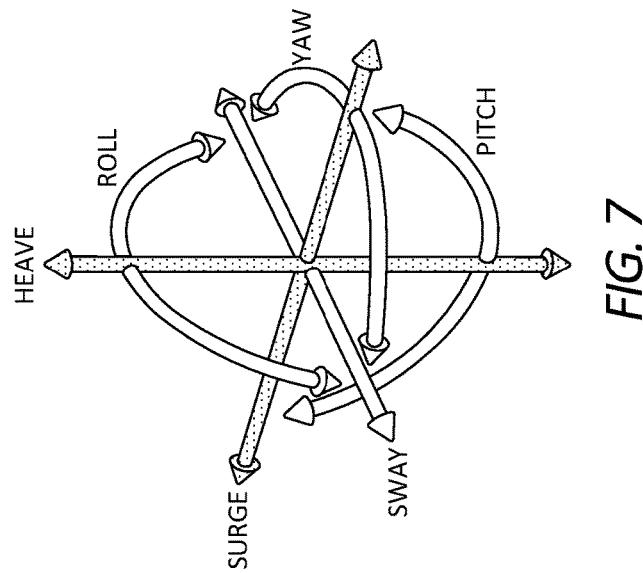
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The wrist 606 can have any of a variety of configurations. In general, the wrist 606 comprises a joint configured to allow pivoting movement of the end effector 604 relative to the shaft 602. The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 3600 rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 may also include a plurality of drive cables (obscured in FIG. 6) that form part of a cable driven motion system configured to facilitate movement of (articulate) the end effector 604 relative to the shaft 602. Moving (actuating) the drive cables moves the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. Due to factors such as manufacturing tolerance and precision of measurement devices, the end effector 604 may not be at a precise zero angle relative to the shaft 602 in the unarticulated position, but nevertheless be considered "substantially aligned" thereto. In the articulated position, the longitudinal axes $A_1$, $A_2$ would be angularly offset from each other such that the end effector 604 is at a non-zero angle relative to the shaft 602.

Still referring to FIG. 6, the surgical tool 600 may be supplied with electrical power (current) via a power cable 614 coupled to the housing 608. In other embodiments, the power cable 614 may be omitted and electrical power may be supplied to the surgical tool 600 via an internal power source, such as one or more batteries or fuel cells. For purposes of the present description, however, it will be assumed that electrical power is provided to the surgical tool 600 via the power cable 614. In either case, the surgical tool 600 may alternatively be characterized and otherwise referred to herein as an "electrosurgical instrument" capable of providing electrical energy to the end effector 604.

The power cable 614 may place the surgical tool 600 in communication with a generator 616 that supplies energy, such as electrical energy (e.g., radio frequency energy), ultrasonic energy, microwave energy, heat energy, or any combination thereof, to the surgical tool 600 and, more particularly, to the end effector 604. Accordingly, the generator 616 may comprise a radio frequency (RF) source, an ultrasonic source, a direct current source, and/or any other suitable type of electrical energy source that may be activated independently or simultaneously.

In applications where the surgical tool 600 is configured for bipolar operation, the power cable 614 will include a supply conductor and a return conductor. Current can be supplied from the generator 616 to an active (or source) electrode located at the end effector 604 via the supply conductor, and current can flow back to the generator 616 via a return conductor located at the end effector 604 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 600 is configured for monopolar operation, the generator 616 transmits current through a supply conductor to an active electrode located at the end effector 604, and current is returned (dissipated) through a return electrode (e.g., a grounding pad) separately located on a patient's body.

Figure 8:
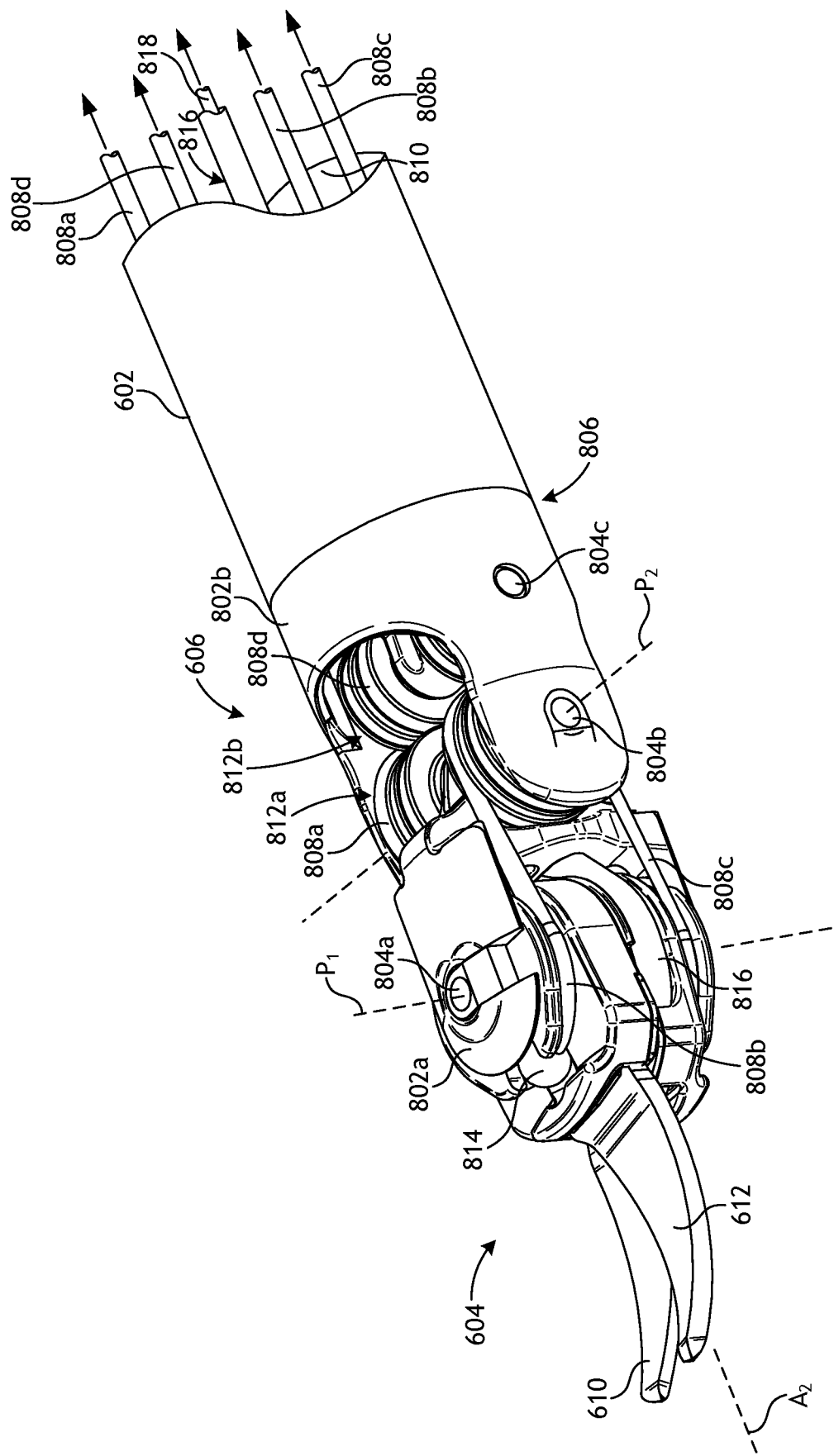
FIG. 8 is an enlarged isometric view of the distal end of the surgical tool of FIG. 1.

FIG. 8 is an enlarged isometric view of the distal end of the surgical tool 600 of FIG. 6. More specifically, FIG. 8 depicts enlarged views of the end effector 604 and the wrist 606, with the end effector 604 in the unarticulated position. The wrist 606 operatively couples the end effector 604 to the shaft 602. To accomplish this, the wrist 606 includes a distal clevis 802a and a proximal clevis 802b. The end effector 604 (i.e., the jaws 610, 612) is rotatably mounted to the distal clevis 802a at a first axle 804a, the distal clevis 802a is rotatably mounted to the proximal clevis 802b at a second axle 804b, and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604. In the illustrated embodiment, the jaws 610, 612 are mounted at the first pivot axis $P_1$, thereby allowing the jaws 610, 612 to pivot relative to each other to open and close the end effector 604 or alternatively pivot in tandem to articulate the orientation of the end effector 604.

A plurality of drive cables, shown as drive cables 808a, 808b, 808c, and 808d, extend longitudinally within a lumen 810 defined by the shaft 602 and pass through the wrist 106 to be operatively coupled to the end effector 604. While four drive cables 808a-d are depicted in FIG. 8, more or less than four drive cables 808a-d may be included, without departing from the scope of the disclosure.

The drive cables 808a-d form part of the cable driven motion system briefly described above, and may be referred to and otherwise characterized as cables, bands, lines, cords, wires, ropes, strings, twisted strings, elongate members, etc. The drive cables 808a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 810 can be a single lumen, as illustrated, or can alternatively comprise a plurality of independent lumens that each receive one or more of the drive cables 808a-d.

The drive cables 808a-d extend proximally from the end effector 604 to the drive housing 608 (FIG. 6) where they are operatively coupled to various actuation mechanisms or devices housed (contained) therein to facilitate longitudinal movement (translation) of the drive cables 808a-d within the lumen 810. Selective actuation of all or a portion of the drive cables 808a-d causes the end effector 604 (e.g., one or both of the jaws 610, 612) to articulate (pivot) relative to the shaft 602. More specifically, selective actuation causes a corresponding drive cable 808a-d to translate longitudinally within the lumen 810 and thereby cause pivoting movement of the end effector 604. One or more drive cables 808a-d, for example, may translate longitudinally to cause the end effector 604 to articulate (e.g., both of the jaws 610, 612 angled in a same direction), to cause the end effector 604 to open (e.g., one or both of the jaws 610, 612 move away from the other), or to cause the end effector 604 to close (e.g., one or both of the jaws 610, 612 move toward the other).

Moving the drive cables 808a-d can be accomplished in a variety of ways, such as by triggering an associated actuator or mechanism operatively coupled to or housed within the drive housing 608 (FIG. 6). Moving a given drive cable 808a-d constitutes applying tension (i.e., pull force) to the given drive cable 808a-d in a proximal direction, which causes the given drive cable 808a-d to translate and thereby cause the end effector 604 to move (articulate) relative to the shaft 602.

The wrist 606 includes a first plurality of pulleys 812a and a second plurality of pulleys 812b, each configured to interact with and redirect the drive cables 808a-d for engagement with the end effector 604. The first plurality of pulleys 812a is mounted to the proximal clevis 802b at the second axle 804b and the second plurality of pulleys 812b is also mounted to the proximal clevis 802b but at a third axle 804c located proximal to the second axle 804b. The first and second pluralities of pulleys 812a,b cooperatively redirect the drive cables 808a-d through an "S" shaped pathway before the drive cables 808a-d are operatively coupled to the end effector 604.

In at least one embodiment, one pair of drive cables 808a-d is operatively coupled to each jaw 610, 612 and configured to "antagonistically" operate the corresponding jaw 610, 612. In the illustrated embodiment, for example, a first connector 814 couples the first and second drive cables 808a,b, and a second connector (occluded) similarly couples the third and fourth drive cables 808c,d.

Actuation of the first drive cable 808a acts on the first connector 814 and thereby pivots the second jaw 612 about the first pivot axis $P_1$ toward the open position. In contrast, actuation of the second drive cable 808b also acts on the first connector 814 but pivots the second jaw 812 about the first pivot axis $P_1$ in the opposite direction and toward the closed position. Similarly, actuation of the third drive cable 808c acts on the second connector (occluded) and thereby pivots the first jaw 610 about the first pivot axis $P_1$ toward the open position, while actuation of the fourth drive cable 808d also acts on the second connector (occluded) but pivots the first jaw 610 about the first pivot axis $P_1$ in the opposite direction and toward the closed position.

Accordingly, the drive cables 808a-d may be characterized or otherwise referred to as "antagonistic" cables that cooperatively (yet antagonistically) operate to cause relative or tandem movement of the first and second jaws 610, 612. When the first drive cable 808a is actuated (moved), the second drive cable 808b naturally follows as coupled to the first drive cable 808a at the first connector 814, and vice versa. Similarly, when the third drive cable 808c is actuated, the fourth drive cable 808d naturally follows as coupled to the third drive cable 808c at the second connector (occluded), and vice versa.

The first connector 814 and the occluded second connector may comprise any attachment mechanism capable of coupling the first and second drive cables 808a,b and the third and fourth drive cables 808c,d, respectively, such that movement (actuation) of one drive cable correspondingly moves the other, and vice versa. In the illustrated embodiment, for example, the first connector 814 (and the occluded second connector) may comprise a ball crimp. In other embodiments, however, the first connector 814 (and the occluded second connector) may include, but is not limited to, a welded attachment, a brazed attachment, an adhesive bond, a mechanical fastener, or any combination thereof.

The surgical tool 600 may also include an electrical conductor 816 that supplies electrical energy to the end effector 604, thereby converting the surgical tool 600 into an "electrosurgical instrument". Similar to the drive cables 808a-d, the electrical conductor 816 extends longitudinally within the lumen 810 and passes through the wrist 106 to be operatively (and electrically) coupled to the end effector 604. In some embodiments, the electrical conductor 816 and the power cable 614 (FIG. 6) may comprise the same structure. In other embodiments, however, the electrical conductor 816 may be electrically coupled to the power cable 614. In yet other embodiments, the electrical conductor 816 may extend to the drive housing 608 (FIG. 6) where it is electrically coupled to an internal power source, such as batteries or fuel cells.

The electrical conductor 816 may comprise a supply conductor 818 encapsulated by an insulating cover (e.g., an insulated wire). In the illustrated embodiment, the end effector 604 is configured for monopolar operation. Accordingly, electrical energy is transmitted by the supply conductor 818 to the end effector 604, which acts as an active (or source) electrode. In at least one embodiment, the electrical energy may comprise radio frequency ("RF") energy exhibiting a frequency between about 100 kHz and 1 MHz. Low frequency RF energy causes ionic agitation or friction, in effect resistive heating, thereby increasing the temperature of target tissue. Accordingly, electrical energy supplied to the end effector 604 is converted to heat and transferred to adjacent tissue to cut, cauterize, and/or coagulate the tissue (dependent upon the localized heating of the tissue), and thus may be particularly useful for sealing blood vessels or diffusing bleeding. Electrical energy is then returned from the tissue through a return electrode, which typically comprises a grounding pad separately located on a patient's body.

Monopolar electrosurgical instruments, however, have at least one downside that is especially evident when used in laparoscopic procedures. Unless properly insulated, the active electrode of the end effector 604 may inadvertently arc between conductive materials, such as electrically conductive component parts of the end effector 604 (e.g., the distal clevis 802a). In such cases, stray electrical current may be transmitted to unseen and/or untargeted tissue, which could potentially injure the patient by causing unintended or unknown damage or ablations to the patient's tissue. According to embodiments of the present disclosure, the end effector 604 may be designed and otherwise configured to insulate the electrical conductor 816 from conductive materials that form part of the end effector 604.

Figure 9:
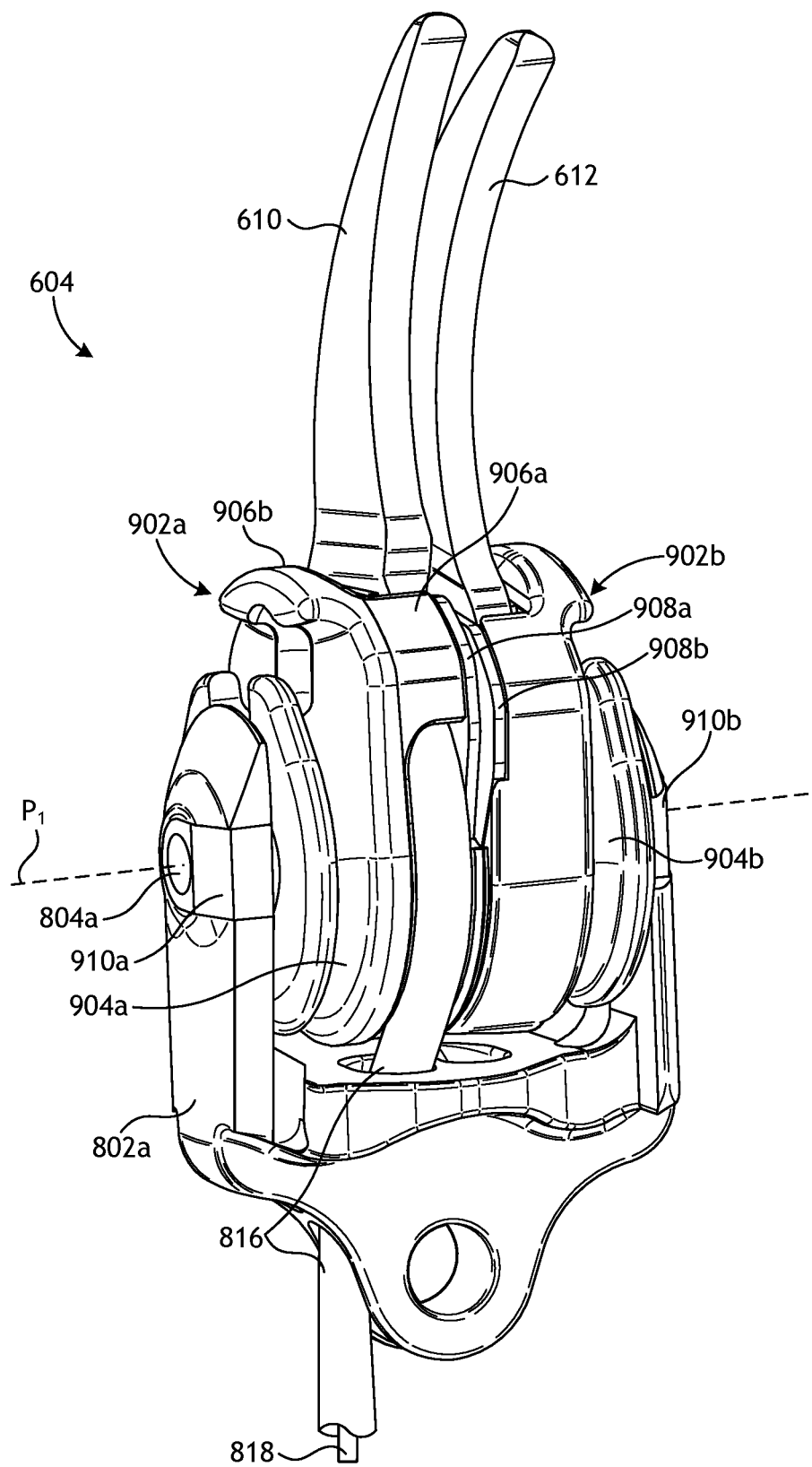
FIG. 9 is an enlarged view of the end effector 604 of FIG. 8.

FIG. 9 is an enlarged view of the end effector 604 of FIG. 8. As mentioned above, the end effector 604 includes the first and second jaws 610, 612 rotatably mounted to the distal clevis 802a at the first axle 804a. A portion of the electrical conductor 816 is also depicted extending to the end effector 604 to provide electrical energy to the first jaw 610 via the insulated supply conductor 818. The drive cables 808a-d of FIG. 8 are omitted to enable better viewing of the component parts of the end effector 604.

As illustrated in FIG. 9, the end effector 604 further includes a first jaw holder 902a and a second jaw holder 902a laterally offset from the first jaw holder 902a. The first jaw holder 902a is mounted to the first axle 804a and configured to receive and seat the first jaw 610 such that movement (rotation) of the first jaw holder 902a about the first pivot axis $P_1$ correspondingly moves (rotates) the first jaw 610. The first jaw holder 902a may also provide and otherwise define a first pulley 904a configured to receive and seat one or more drive cables, such as the third and fourth drive cables 808c,d of FIG. 8, to effect such movement (rotation). The second jaw holder 902b is similarly mounted to the first axle 804a and is configured to receive and seat the second jaw 612 such that movement (rotation) of the second jaw holder 902b about the first pivot axis $P_1$ correspondingly moves (rotates) the second jaw 612. The second jaw holder 902b may also provide and otherwise define a second pulley 904b configured to receive and seat one or more drive cables, such as the first and second drive cables 808a,b of FIG. 8, to effect such movement (rotation).

The term "jaw holder," as used herein, is intended to apply to a variety of types of end effectors having opposing jaws or blades that are movable relative to one another. In the illustrated embodiment, the jaws 610, 612 comprise opposing scissor blades of a surgical scissors end effector. Accordingly, the jaw holders 902a,b may alternately be referred to as "blade holders". In other embodiments, however, the jaws 610, 612 may alternatively comprise opposing jaws used in a grasper end effector, or the like, and the term "jaw holder" similarly applies, without departing from the scope of the disclosure. Moreover, the term "holder" in "jaw holder" may be replaced with "mount," "drive member," or "actuation member."

The first and second jaw holders 902a,b may be made of any electrically insulating or non-conductive material. Suitable non-conductive materials include, but are not limited to, a ceramic (e.g., zirconia, alumina, aluminum nitride, a silicate, silicon nitride, etc.), high temperature and high strength plastics, a thermoplastic or thermosetting polymer (e.g., polyether ether ketone, ULTEM™, VESPEL®, a polyphenylsulfone, a polysulfone, RADEL®, a polyamide-imide, a polyimide, an epoxy, etc.), a composite material (e.g., fiberglass), hard rubber (e.g., ebonite), or any combination thereof. Alternatively, the proximal region of the jaws 610, 612 may be coated in a nonconductive material (e.g., ceramic) to isolate the proximal regions of the jaws 610, 612 from the jaw holders 902a,b that isolated the jaws 610, 612 from the rest of the wrist components, thus allowing these wrist components to be constructed out of a tradition conductive material such as stainless steel.

In some embodiments, the first jaw holder 902a may comprise a monolithic structure made of a single non-conductive material. In other embodiments, however, the first jaw holder 902a may comprise a first portion 906a and a second portion 906b coupled to the first portion 906a. In the illustrated embodiment, the first portion 906a may be configured to receive the first jaw 610 and the second portion 906b may provide the first pulley 904a. In some embodiments, the first and second portions 906a,b may be made of dissimilar materials. In such embodiments, for example, the first portion 906a may be made of a non-conductive material (e.g., ceramic or a polymer) and the second portion 906b may be made of a dissimilar non-conductive material or alternatively a conductive material. In other embodiments, however, the first and second portions 906a,b may be made of dissimilar non-conductive materials. In such embodiments, for example, the first portion 906a may be made of ceramic, and the second portion 906b may be made of a plastic, which may be overmolded onto the first portion 906a and otherwise coupled thereto. As will be appreciated, the foregoing alternative embodiments may be equally applicable to the second jaw holder 902b, without departing from the scope of the disclosure.

The end effector 604 may further include at least one spacer that interposes the first and second jaw holders 902a,b. In the illustrated embodiment, the end effector 604 includes a first spacer 908a configured to be received by the first jaw holder 902a and a second spacer 908b configured to be received by the second jaw holder 902b. During operation, the first and second spacers 908a,b may slidingly engage (rub against) each other as the opposing jaws 610, 612 rotate about the first pivot axis $P_1$ between open and closed positions.

To reduce friction and drag force generated between the two structures, the first and second spacers 908a,b may be made of a lubricious (e.g., slippery or slick) material. Suitable lubricious materials include, but are not limited to, nylon, polished metal, a smooth plastic, or any combination thereof. In other embodiments, however, the first and second spacers 908a,b may be coated with a lubricious substance or material such as, but not limited to, oil, graphite, TEFLON™, silicone, or any combination thereof.

The end effector 604 may further include a first end cap 910a and a second end cap 910b (mostly occluded in FIG. 9). As discussed in more detail below, the first and second end caps 910a,b may be configured to mount the first axle 804a to the distal clevis 802a.

Figure 10B:
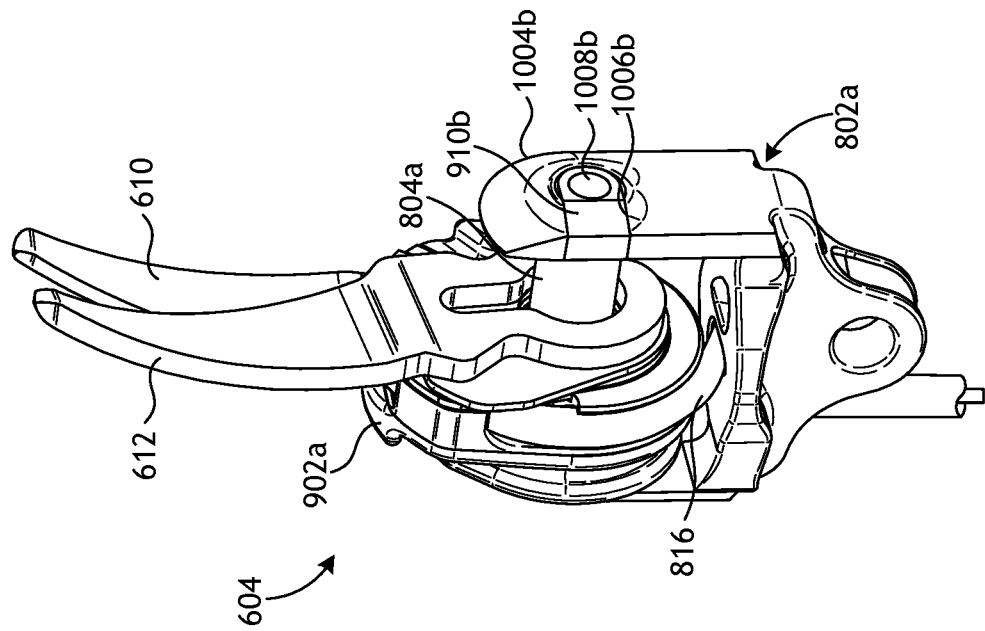
FIG. 10B is an isometric view of the end effector of FIG. 9 without the second jaw holder.
Figure 10A:
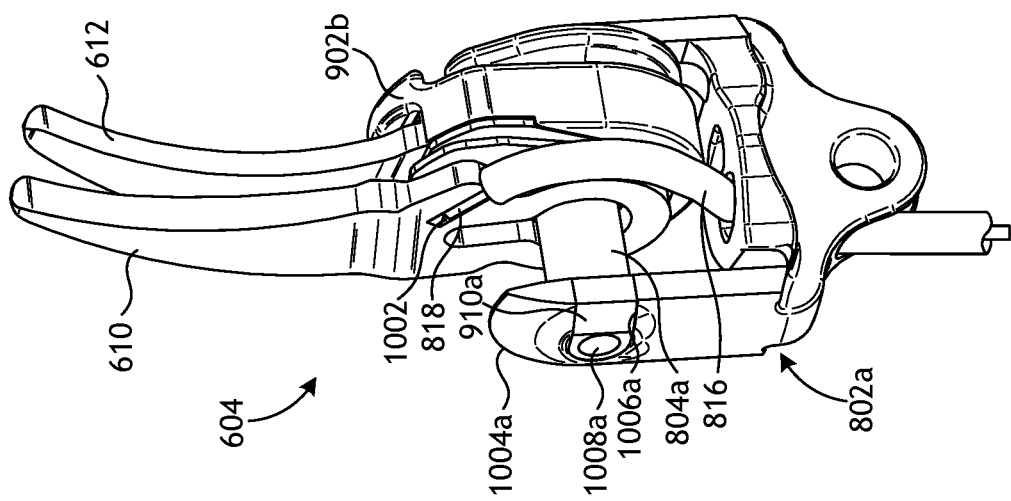
FIG. 10A is an isometric view of the end effector of FIG. 9 without the first jaw holder.

FIG. 10A is an isometric view of the end effector 604 without the first jaw holder 902a, and FIG. 10B is an isometric view of the end effector 604 without the second jaw holder 902b. In FIG. 10A, the electrical conductor 816 is shown extending to the end effector 604 to provide electrical energy to the first jaw 610 via the insulated supply conductor 818. The supply conductor 818 may be received within a pocket 1002 defined in the first jaw 610. In some embodiments, the supply conductor 818 may be resistance welded or soldered to the pocket 1002. Electrical energy conveyed through the supply conductor 818 will be transferred to the first jaw 610 at the pocket 1002. Accordingly, the first jaw 610 may effectively be characterized as an active electrode for the end effector 604, and electrical energy transmitted to the first jaw 610 is transmitted to the second jaw 612 by virtue of contact between the jaws 610, 612.

FIGS. 10A and 10B also depict how the first axle 804a may be mounted to the distal clevis 802a. As illustrated, the distal clevis 802a includes a first distally-extending arm 1004a (FIG. 10A) and a second distally-extending arm 1004b (FIG. 10B). The first arm 1004a defines a first slot 1006a (FIG. 10A) configured to receive and secure the first end cap 910a, and the second arm 1004b defines a second slot 1006b (FIG. 10B) configured to receive and secure the second end cap 910b. A first end 1008a (FIG. 10A) of the first axle 804a may be received by the first end cap 910a and a second end 1008b (FIG. 10B) of the first axle 804a may be received by the second end cap 910b. Once the first and second ends 1008a,b are received by the first and second end caps 910a,b, respectively, the end caps 910a,b may be received and secured within the first and second slots 100a6a,b, respectively.

Figure 11B:
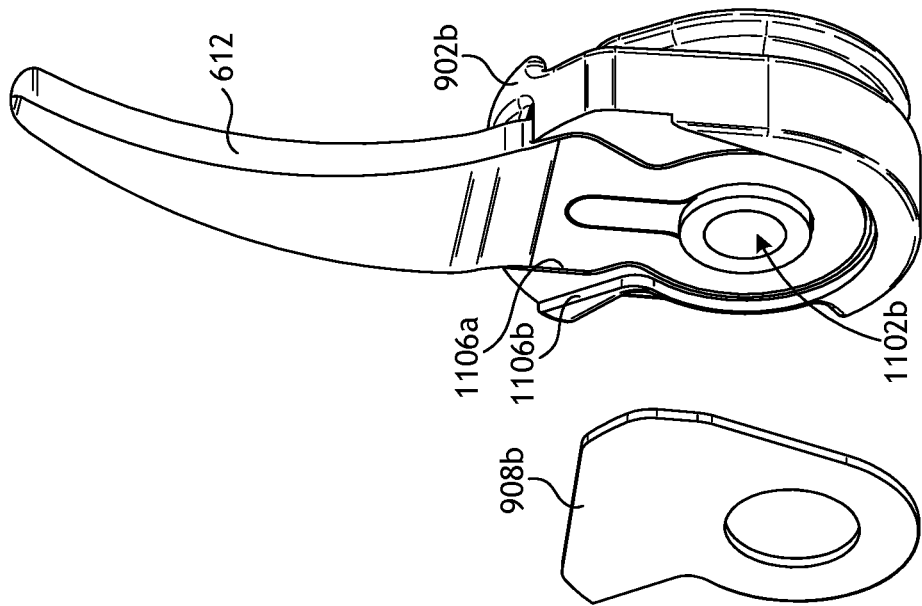
FIG. 11B is a partially exploded view of the second jaw holder and corresponding second spacer.
Figure 11A:
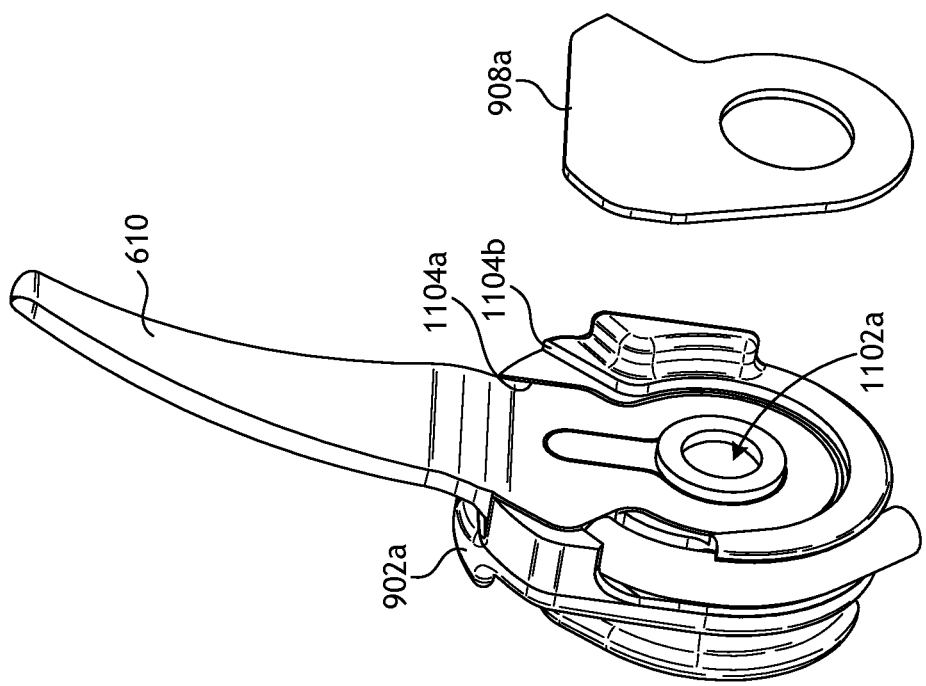
FIG. 11A is a partially exploded view of the first jaw holder and corresponding first spacer.

FIG. 11A is a partially-exploded view of the first jaw holder 902a and corresponding first spacer 908a, and FIG. 11B is a partially-exploded view of the second jaw holder 902b and corresponding second spacer 908b. As illustrated, the first and second spacers 908a,b may be plate-like structures. In one or more embodiments, the spacers 908a,b may be made of any of the non-conductive materials mentioned herein.

In FIG. 11A, the first jaw holder 902a defines a central aperture 1102a configured to receive the first axle 804a (FIGS. 9 and 10A-10B) to rotatably mount the first jaw holder 902a thereto. The first jaw holder 902a also defines a first recess 1104a configured to receive and seat the first jaw 610 such that movement (rotation) of the first jaw holder 902a will correspondingly move (rotate) the first jaw 610. A second recess 1104b may also be defined by the first jaw holder 902a to receive and seat the first spacer 908a.

In FIG. 11B, the second jaw holder 902b defines a central aperture 1102b configured to receive the first axle 804a (FIGS. 9 and 10A-10B) to rotatably mount the second jaw holder 902b thereto. The second jaw holder 902b also defines a first recess 1106a configured to receive and seat the second jaw 612 such that movement (rotation) of the second jaw holder 902b will correspondingly move (rotate) the second jaw 612. A second recess 1104b may also be defined by the second jaw holder 902b to receive and seat the second spacer 908b.

Figure 12:
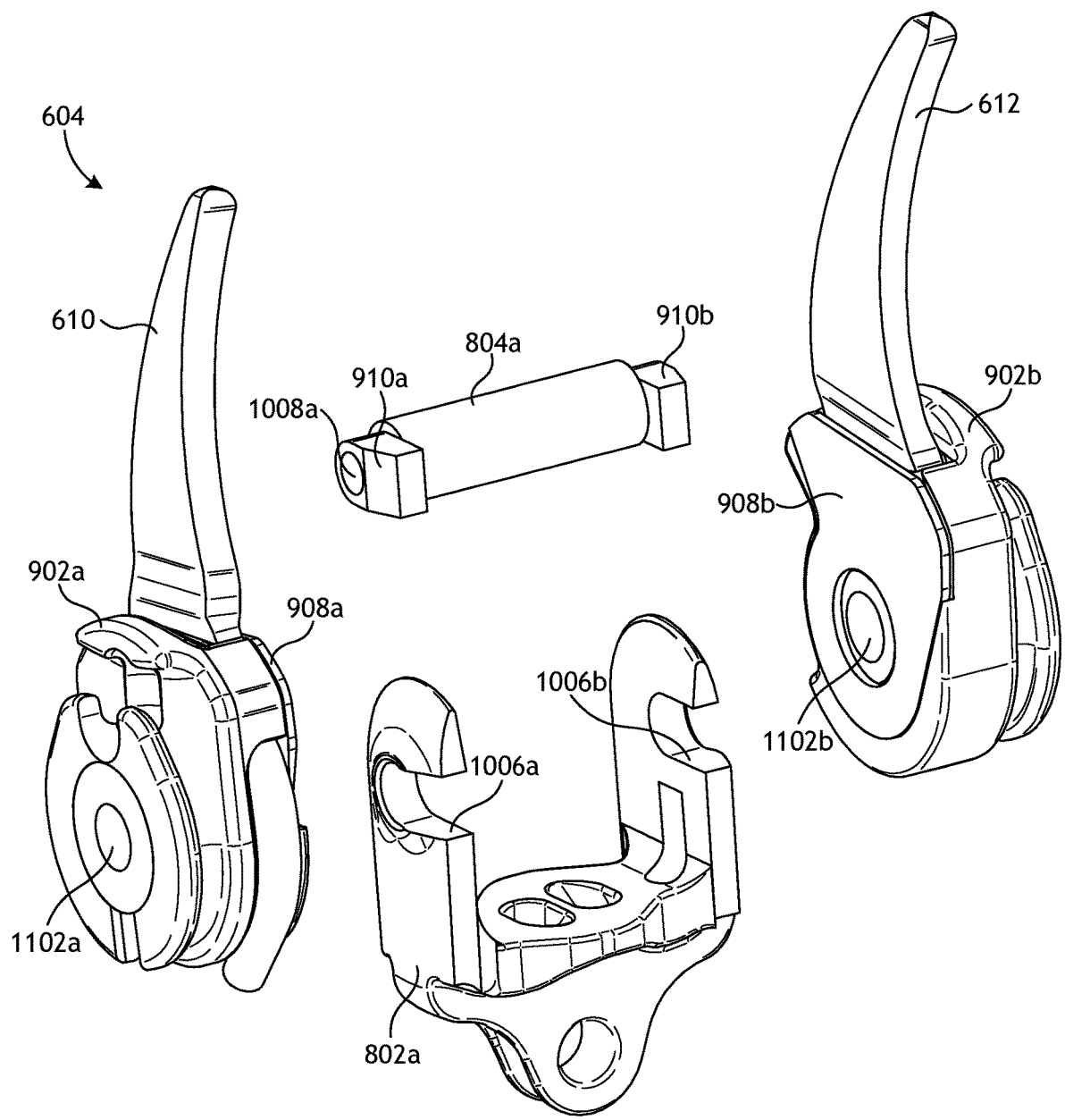
FIG. 12 is an isometric exploded view of the end effector of FIG. 8.

FIG. 12 is an exploded view of the end effector 604 of FIG. 8. To assemble the end effector 604, the first axle 804a is first extended through the central apertures 1102a,b of the first and second jaw holders 902a,b, respectively. The opposing ends 1008a,b (only first end 1008a visible in FIG. 12) of the first axle 804a may then be received by the first and second end caps 910a,b, respectively. In some embodiments, the ends 1008a,b may be press fit into the corresponding end caps 910a,b, such that an interference fit results. In other embodiments, however, the ends 1008a,b may be received by the corresponding end caps 910a,b such that the first axle 804a is rotatably mounted to the end caps 910a,b.

The end caps 910a,b may then be received and secured within the slots 1006a,b provided on the distal clevis 802a. In some embodiments, the end caps 910a,b may be welded or brazed to the corresponding slots 1006a,b. In such embodiments, the end caps 910a,b may be made of a metal, such as stainless steel or another durable metal that may be welded or brazed to the distal clevis 802a at the slots 1006a,b. The first axle 804a is captured between the two end caps 910a,b and then held into the clevis 802a when the caps 910a,b are welded to the corresponding slots 1006a,b. During this welding process, the end caps 910a,b are held in contact with the end surfaces of the first axle 804a, thus eliminating any part tolerances and subsequent gaps. In other embodiments, the end caps 910a,b may secured within the corresponding slots 1006a,b by other means, such as by using one or more mechanical fasteners, an interference or snap fit, or by orbital riveting of the outer surface of the end caps 910a,b.

Because several component parts of the end effector 604 are made of non-conductive materials, the monopolar electrical energy supplied to the jaws 610, 612 may be effectively isolated from electrically-conductive parts of the end effector 604. For example, the first axle 804a, one or both of the jaw holders 902a,b, and one or both of the spacers 908a,b may each be made of any of the non-conductive materials mentioned herein, which electrically isolates the distal clevis 802a from the monopolar electrical energy. Consequently, the electrical energy supplied to the jaws 610, 612 cannot inadvertently arc to the distal clevis 802a through these parts, which helps reduce the occurrence of unintended or unknown damage or ablations to patient tissue. This also eliminates the need for a separate insulative sleeve to be applied over the entire end effector before use.

FIG. 13 is an enlarged view of another example end effector 1302 that may be used with the surgical tool 600 of FIG. 6, according to one or more embodiments. Accordingly, in some applications, the end effector 1302 of FIG. 13 may replace the end effector 604 of FIGS. 6 and 8-12. The end effector 1302 may be similar in some respects to the end effector 604 and therefore may be best understood with reference thereto, where like numerals will represent like component not described again.

Similar to the end effector 604 of FIGS. 6 and 8-12, the end effector 1302 includes the first and second jaws 610, 612 rotatably mounted to the distal clevis 802a at the first axle 804a. The end effector 1302 also includes the first and second jaw holders 902a,b that receive and seat the first and second jaws 610, 612, respectively, for corresponding movement (rotation) therewith. Furthermore, the end effector 1302 also includes a first end cap 1304a and a second end cap 1304b (occluded in FIG. 13; see FIGS. 14 and 15). The first and second end caps 1304a,b may be configured to mount the first axle 804a to the distal clevis 802a.

A portion of the electrical conductor 816 is also depicted extending to the end effector 1302 to provide electrical energy to the end effector 1302 via the insulated supply conductor 818. Unlike the end effector 604 of FIGS. 8-12, however, the electrical conductor 816 extends to the first axle 804a and transfers electrical energy directly to the jaws 610, 612 via a contact plate (not shown) mounted to the first axle 804a.

FIG. 14 is a cross-sectional front view of the end effector 1302 of FIG. 13. As illustrated, the electrical conductor 816 extends into a channel 1402 defined in the first axle 804a and an end of the supply conductor 818 extends distally to engage (or come into close contact with) a contact plate 1404 mounted to the first axle 804a. The top surface of the contact plate 1404 is positioned and otherwise arranged to transfer electrical energy from the supply conductor 818 to the jaws 610, 612.

In at least one embodiment, the first jaw 610 may define a first arcuate bottom surface 1405a and the second jaw 612 may define a second arcuate bottom surface 1405b. The arcuate bottom surfaces 1405a,b may be configured to slidingly engage the top surface of the contact plate 1404 as the jaws 610, 612 move between open and closed positions. In other embodiments, however, sliding contact between the opposing structures need not occur since the voltages run through the supply conductor 818 may be sufficient to arc across a small gap between the bottom surfaces 1405a,b and the top surface of the contact plate 1404.

FIG. 14 also depicts how the first axle 804a may be mounted to the distal clevis 802a. The first arm 1004a defines a first slot 1406a configured to receive and secure the first end cap 1304a, and the second arm 1004b defines a second slot 1406b configured to receive and secure the second end cap 1304b. A first end 1408a of the first axle 804a may be received by the first end cap 1304a and a second end 1408b of the first axle 804a may be received by the second end cap 1304b. In at least one embodiment, the first end cap 1304a may provide and otherwise define a first pocket 1410a sized to receive the first end 1408a of the first axle 804a, and the second end cap 1304b may provide and otherwise define a second pocket 1410b sized to receive the second end 1408b of the first axle 804a.

FIG. 15 is an exploded view of the end effector 1302 of FIG. 13. As illustrated, the contact plate 1404 may comprise an arcuate body 1502 that defines a central aperture 1504. On either lateral side of the aperture 1504, the body 1502 provides contact surfaces 1506a and 1506b. During operation, the arcuate bottom surfaces 1405a,b (only the second bottom surface 1405b is visible in FIG. 15) of the jaws 610, 612 may be configured to slidingly engage the contact surfaces 1506a,b. In other embodiments, however, sliding contact between the opposing structures need not occur since the voltages run through the supply conductor 818 may be sufficient to arc across a small gap between the bottom surfaces 1405a,b and the top surface of the contact plate 1404. Moreover, a small gap between the opposing structures may help reduce friction in the assembly.

As best seen in the enlarged, inset graphic of the contact plate 1404, a contact tab 1508 may extend from the body 1502 within the aperture 1504. The contact tab 1508 may provide a location where the supply conductor 818 can engage the contact plate 1404 and thereby transmit electrical energy thereto. In some embodiments, the supply conductor 818 may be resistance welded or soldered to the contact tab 1508. In other embodiments, however, the supply conductor 818 may be in biased engagement with the contact tab 1508 to transmit the electrical energy thereto. In yet other embodiments, the contact tab 1508 may be omitted and the supply conductor 818 may instead be welded or soldered to or in biased engagement with any other portion of the contact plate 1404, without departing from the scope of the disclosure.

To assemble the end effector 1302, the contact plate 1404 may first be mounted to the first axle 804a. In at least one embodiment, the first axle 804a may define or provide a recess 1510 configured to receive the contact plate 1404 such that a flush mounting arrangement results. The electrical conductor 816 may then be inserted into the channel 1402 defined in the first axle 804a and the supply conductor 818 may be placed in engagement (contact) with the contact plate 1404 (e.g., the contact tab 1508) to facilitate transfer of electrical energy.

The first and second jaw holders 902a,b may then be mounted to the first axle 804a at the central apertures 1102a,b, respectively. The first and second jaw holders 902a,b may be brought into close lateral engagement such that the arcuate bottom surfaces 1405a,b (only the second bottom surface 1405b is visible in FIG. 15) come into contact with (or close proximity without engagement) the contact surfaces 1506a,b, respectively, of the contact plate 1404.

The opposing ends 1408a,b of the first axle 804a may then be received by the first and second end caps 1304a,b, respectively. In some embodiments, the ends 1408a,b may be press fit into the corresponding pockets 1410a,b (only the second pocket 1410b is visible in FIG. 15) of the end caps 1304a,b such that an interference fit results. In other embodiments, or in addition thereto, the pockets 1410a,b may provide an inner profile configured to mate with a corresponding outer profile provided by each opposing end 1408a,b. In the illustrated embodiment, for example, the pockets 1410a,b may define and otherwise provide a flat inner surface 1512 configured to mate with a corresponding flat outer surface 1514 defined by each end 1408a,b. The mated relationship between the ends 1408a,b and the end caps 1304a,b may prove advantageous in preventing the first axle 804a from rotating during operation.

The end caps 1304a,b may then be received and secured within the slots 1406a,b provided on the distal clevis 802a. In some embodiments, the end caps 1304a,b may be welded or brazed to the corresponding slots 1406a,b. In such embodiments, the end caps 1304a,b may be made of a metal, such as stainless steel or another durable metal that may be welded or brazed to the distal clevis 802a. The width of the first axle 804a may be less than the width of the opening in the distal clevis 802a, such that during the welding process the end caps 1304a,b press the jaw holders 902a,b against one another. In other embodiments, the end caps 1304a,b may secured within the corresponding slots 1406a,b by other means, such as by using one or more mechanical fasteners or through an interference fit, or by orbital riveting of the outer surface of the end caps 910a,b, without departing from the scope of the disclosure.

According to the present disclosure, one or more component parts of the end effector 1302 are made of non-conductive materials that effectively isolate the distal clevis 802a from the monopolar energy conducted through the electrical conductor 816 to the jaws 610, 612. For example, one or more of the first axle 804a, the first jaw holder 902a, and the second jaw holder 902b may be made of any of the non-conductive materials mentioned herein. Consequently, the electrical energy supplied to the jaws 610, 612 via the contact plate 1404 cannot inadvertently arc to the distal clevis 802a through these parts, which helps reduce the occurrence of unintended or unknown damage or ablations to the patient's tissue.

FIG. 16 is an isometric view of a portion of another example end effector 1602, according to one or more embodiments. More specifically, FIG. 16 depicts a jaw 1604 and a corresponding jaw holder 1606 of the end effector 1602. While not shown, the end effector 1602 may further include a second jaw and a corresponding second jaw holder configured to operate in tandem with the illustrated jaw 1604 as a tissue grasper, for example. As will be appreciated, the following description of the jaw 1604 and the jaw holder 1606 may be equally applicable to the opposing, non-illustrated second jaw and corresponding second jaw holder. Accordingly, the end effector 1602 may be similar in some respects to the end effector 604 of FIGS. 8-12 and, in some applications, the end effector 1602 may replace the end effector 604 and may be used with the surgical tool 600 of FIG. 6.

The jaw holder 1606 secures the jaw 1604 such that movement (rotation) of the jaw holder 1606 during operation correspondingly moves (rotates) the jaw 1604. As illustrated, the jaw holder 1606 provides and otherwise defines a pulley 1608 configured to receive and seat one or more drive cables, such as the first and second drive cables 808a,b of FIG. 8. A pocket 1610 may be defined on the pulley 1608 to receive and seat the connector 814, which couples the drive cables 808a,b to effect movement (rotation) of the jaw holder 1606, as generally described above. The jaw holder 1606 also defines a central aperture 1612 configured to receive an axle (e.g., the first axle 804a of FIGS. 9 and 10A-10B) to rotatably mount the jaw holder 1606 thereto.

A portion of an electrical conductor 1614 is also depicted extending to the end effector 1602 to provide electrical energy to the end effector 1602 (i.e., the jaw 1604). The electrical conductor 1614 may be similar to (or the same as) the electrical conductor 816 of FIG. 9 and, therefore, may include a supply conductor 1616 encased in an insulative covering. The supply conductor 1616 may be electrically coupled to the jaw 1604, thereby making the jaw an active (or source) electrode for the end effector 1602. In some embodiments, the end effector 1602 is configured for monopolar operation using only the electrical conductor 1614. In other embodiments, however, end effector 1602 may be configured for bipolar operation. In such embodiments, the end effector 1602 may include a second electrical conductor extending to and electrically coupling to a second jaw (not shown) of the end effector 1602, and thereby making the second jaw a return electrode.

The jaw holder 1606 may be made of any of the electrically insulating or non-conductive materials mentioned herein. In some embodiments, the jaw holder 1606 may comprise a monolithic structure made of a single non-conductive material. In other embodiments, however, the jaw holder 1606 may comprise a first portion 1618a and a second portion 1618b coupled to the first portion 1618a. The first portion 1618a may be configured to receive and secure the jaw 1604 and provide the pulley 1608, and the second portion 1618b may be configured to fully encapsulate and insulate the supply conductor 1616 at the jaw 1604. The first portion 1618a may be molded (e.g., overmolded) onto the jaw 1604 via a first injection molding shot, and the second portion 1618b may be overmolded onto the first portion 1618a via a second injection molding shot. In some embodiments, the first and second portions 1618a,b may be made of the same non-conductive material, but could alternatively be made of dissimilar non-conductive materials, without departing from the scope of the disclosure.

Since the portions 1618a,b of the jaw holder 1606 are made of non-conductive materials and are formed to fully insulate the supply conductor 1616 at the jaw 1604, the electrical energy supplied to the jaw 1604 may be effectively isolated from adjacent electrically-conductive parts of the end effector 1602, such as an axle (e.g., the first axle 804a of FIG. 8), the drive cables 808a,b, or a clevis (e.g., the distal clevis 802a of FIG. 8). Consequently, the electrical energy supplied to the jaw 1604 may have a reduced the risk of inadvertent tissue damage due to unintended current leakage to electrically-conductive parts of the end effector 1602. Additionally, this method fully encapsulates the assembly, and reduces the number of parts, interfaces, and possible crevices where biomaterials may gather. Consequently, this should make the part much easier to clean and sterilize.

FIGS. 17, 18A-18B, 19, and 20A-20B illustrate progressive views of an example process of manufacturing the portion of the end effector 1602 of FIG. 16, according to one or more embodiments. FIG. 17 is an isometric side view of the jaw 1604 of FIG. 16. The jaw 1604 may be made of a variety of electrically-conductive materials, such as metal. In at least one embodiment, the jaw 1604 may be made of s are 17-4 stainless steel, but could alternatively be made of any conductive, high strength material that is resistant to chemical attack, such as a high strength stainless steel. In some applications, the jaw 1604 may be coated to impart specific properties. For example, the jaw 1604 may be coated to provide a release layer or to prevent corrosion. The jaw 1604 may be machined from a larger piece of material or may alternatively be manufactured, such as through metal injection molding (MIM), machining, stamping, 3D printing, or any combination thereof.

As illustrated, the jaw 1604 includes a tissue engagement portion 1702, a shank 1704 that extends from the tissue engagement portion 1702, and a contact plate 1706 coupled to or forming part of the shank 1704. The contact plate 1706 may provide a location where the supply conductor 1616 (FIG. 16) is coupled to the jaw 1604 to convey electrical energy thereto. The contact plate 1706 may define a pinhole 1708 through which the supply conductor 1616 may extend to access the contact plate 1706.

In some embodiments, the jaw 1604 may also define a through hole 1710 and a central aperture 1712. The through hole 1710 may prove advantageous in helping couple the supply conductor 1616 to the contact plate 1706 and in helping lock the jaw 1604 to the jaw holder 1606 (FIG. 16), as discussed more below. The central aperture 1712 may be configured to co-axially align with the central aperture 1612 (FIG. 16) of the jaw holder 1606 to receive an axle (e.g., the first axle 804a of FIGS. 9 and 10A-10B) therethrough.

FIGS. 18A and 18B are front and back views, respectively, of the first portion 1618a of the jaw holder 1606 following a first injection molding process, according to one or more embodiments. The first portion 1618a may be formed over a portion of the shank 1704 and the contact plate 1706. The first injection molding process may alternately be referred to as a first "overmold shot."

In FIG. 18A, the first portion 1618a provides and otherwise defines a cable passage 1802 that communicates with the contact plate 1706 via the pinhole 1708. The electrical conductor 1614 (FIG. 16) may be routed through the cable passage 1802 to allow the supply conductor 1616 (FIG. 16) to electrically communicate with (i.e., transmit electrical energy to) the contact plate 1706. In some embodiments, one or more retention features 1804 may be provided in the cable passage 1802 to help capture the electrical conductor 1614, as discussed in more detail below.

In FIG. 18B, the first portion 1618a may further provide an access passage 1806 eccentric to the central aperture 1612. The access passage 1806 communicates with the through hole 1710 (FIG. 18A) defined in the jaw 1604. During the first overmold shot, the access passage 1806 can be used to locate and align the jaw to the plastic tooling, and thus operates as a "tooling shut off." Moreover, the access passage 1806 and the through hole 1710 cooperatively facilitate access to the contact plate 1706, which may help couple the supply conductor 1616 to the contact plate 1706, as described herein. Accordingly, the access passage 1806 may operate as an "electrode access point." Once the part is overmolded in a second overmolding step (discussed below), the access passage 1806 may help provide a robust mechanical interlock, and this operates as an "interlock channel."

FIG. 19 depicts the electrical conductor 1614 received within the first portion 1618a of the jaw holder 1606. Following the first overmold shot that produces the first portion 1618a, the electrical conductor 1614 may be coupled to and placed in electrical communication with the jaw 1604. More specifically, the electrical conductor 1614 may be routed through and received by the cable passage 1802. A portion of the insulation layer may be stripped from the electrical conductor 1614 to expose the supply conductor 1616, and the exposed portion of the supply conductor 1616 may be extended through the pinhole 1708 to access the contact plate 1706.

The supply conductor 1616 may then be coupled to the contact plate 1706, such as through resistance welding or soldering. In some embodiments, resistance welding may be preferred over soldering as it provides a stronger bond without potentially hardening the electrical conductor 1614 as a result of solder wicking. The coaxially aligned through hole 1710 and access passage 1806 allows a resistance welder access for electrodes to form an opposing contact weld.

The retention features 1804 may be configured to engage the outer insulative layer of the electrical conductor 1614 and thereby help retain the electrical conductor 1614 within the cable passage 1802. As illustrated, the retention features 1804 may comprise angled teeth or protrusions that extend radially into the cable passage 1802, but could alternatively comprise any other type of structure capable of gripping the outer surface of the electrical conductor 1614. In operation, the retention features 1804 substantially prevent the electrical conductor 1614 from reversing back through the cable passage 1802. This may prove advantageous in providing strain relief on the electrical conductor 1614 by helping to mitigate strain over several cycles of using the end effector 1602 (FIG. 16). Moreover, the retention features 1804 may prove advantageous in helping prevent the electrical conductor 1614 from moving during a second overmold shot used to form the second portion 1618b (FIGS. 20A and 20B).

FIGS. 20A and 20B are front and back views, respectively, of the end effector 1602 following a second injection molding process that forms the second portion 1618b of the jaw holder 1606, according to one or more embodiments. The second portion 1618b may be formed over the first portion 1618a and the injection pressure may be sized to prevent excess flash. The second injection molding process may alternately be referred to as a second "overmold shot."

As seen in FIG. 20A, during the second overmold shot, the material for the second portion 1618b (e.g., plastic) fills and encapsulates a cavity 2002 that contains the contact plate 1706 (FIG. 19) and the exposed portion of the supply conductor 1616 (FIG. 19). Accordingly, the second overmold shot electrically isolates and insulates the contact plate 1706 and the adjacent supply conductor 1616. Moreover, as seen in FIG. 20B, the second overmold shot may also fill in the access passage 1806. As will be appreciated, filling in the cavity 2002 and the access passage 1806 helps lock the first and second portions 1618a,b together and helps prevent separation.

Accordingly, the second overmold shot encapsulates and electrically isolates the supply conductor 1616 and the jaw 1604 from adjacent electrically-conductive parts of the end effector 1602 (FIG. 16), which decreases the risk of inadvertent arcing due to creepage and clearance failure. The two overmolding shots also help fill in cracks and crevices in the end effector 1602 that might present a bioburden risk.

FIG. 21 is an isometric view of another example end effector 2102 that may be used with the surgical tool 600 of FIG. 6, according to one or more embodiments. Accordingly, in some applications, the end effector 2102 may replace the end effector 604 of FIG. 6. The end effector 2102 may be similar in some respects to the end effector 1602 of FIG. 16 and, therefore, may be best understood with reference thereto. The end effector 2102 includes a jaw 2104 and a corresponding jaw holder 2106. In the illustrated embodiment, the jaw 2104 is in the form of a surgical hook, but might alternatively comprise a surgical spatula or any other type of end effector tool.

The jaw holder 2106 secures the jaw 2104 such that movement (rotation) of the jaw holder 2106 during operation correspondingly moves (rotates) the jaw 2104. As illustrated, the jaw holder 2106 provides and otherwise defines a first pulley 2108a and a second pulley 2108b (partially occluded). Each pulley 2108a,b is configured to receive and seat one or more drive cables. In the illustrated embodiment, for instance, the first pulley 2108a receives the first and second drive cables 808a,b of FIG. 8, and the second pulley 2108b receives the third and fourth drive cables 808c,d of FIG. 8. A pocket 2110 may be defined on the pulley 2108a to receive and seat the connector 814, which couples the first and second drive cables 808a,b to effect movement (rotation) of the jaw holder 2106, as generally described above. A second pocket (not shown) is defined on the opposing side of the end effector 2102 to receive and seat a second connector (not shown) that couples the third and fourth drive cables 808a,b to effect movement (rotation) of the jaw holder 2106.

The jaw holder 2106 also defines a central aperture 2112 configured to receive an axle (e.g., the first axle 804a of FIGS. 9 and 10A-10B) to rotatably mount the jaw holder 2106 thereto.

A portion of an electrical conductor 2114 is also depicted extending to the end effector 2102 to provide electrical energy to the end effector 2102 (i.e., the jaw 2104). The electrical conductor 2114 may be similar to (or the same as) the electrical conductor 816 of FIG. 9 and, therefore, may include a supply conductor 2116 encased in an insulative covering. The supply conductor 2116 may be electrically coupled to the jaw 2104, thereby making the jaw 2104 an active (or source) electrode for the end effector 2102. In the illustrated embodiment, the end effector 2102 is configured for monopolar operation.

Similar to the jaw holder 1606 of FIG. 16, the jaw holder 2106 may be made of any of the electrically insulating or non-conductive materials mentioned herein. In some embodiments, the jaw holder 2106 may comprise a monolithic structure made of a single non-conductive material. In other embodiments, however, the jaw holder 2106 may comprise a first portion 2118a and a second portion 2118b coupled to the first portion 2118a. The first portion 2118a may be configured to receive and secure the jaw 2104 and provide the first pulley 2108a, and the second portion 2118b may be configured to fully encapsulate and insulate the supply conductor 2116 at the jaw 2104 and provide the second pulley 2108b. As described below, the first portion 2118a may be molded (e.g., overmolded) onto the jaw 2104 via a first injection molding process, and the second portion 2118b may be overmolded onto the first portion 2118b via a second injection molding process. In some embodiments, the first and second portions 2118a,b may be made of the same non-conductive material, but could alternatively be made of dissimilar non-conductive materials, without departing from the scope of the disclosure.

Since the portions 2118a,b of the jaw holder 2106 are made of non-conductive materials and are formed to fully insulate the supply conductor 2116 at the jaw 2104, the electrical energy supplied to the jaw 2104 may be effectively isolated from adjacent electrically-conductive parts of the end effector 2102, such as an axle (e.g., the first axle 804a of FIG. 8), the drive cables 808a-d, or a clevis (e.g., the distal clevis 802a of FIG. 8). Consequently, the electrical energy supplied to the jaw 2104 may reduce the risk of inadvertent tissue damage due to unintended current leakage to electrically-conductive parts of the end effector 2102. Additionally, this method fully encapsulates the assembly, and reduces the number of parts, interfaces, and possible crevices where biomaterials may gather. Consequently, this should make the part much easier to clean and sterilize.

FIGS. 22, 23, 24A-24B, 25, and 26A-26B illustrate progressive views of an example process of manufacturing the end effector 2102 of FIG. 21, according to one or more embodiments. FIG. 22 is an isometric side view of the jaw 2104 of FIG. 21. As illustrated, the jaw 2104 includes a hook member 2202 and an isolator 2204. The hook member 2202 may include a shank 2206 sized to be received within a central passageway 2208 defined through the isolator 2204. In at least one embodiment, the end of the shank 2206 may define a planar surface 2210. In some embodiments, the isolator 2204 may provide and otherwise define a mold profile 2212 that may help secure the jaw 2104 to the jaw holder 2106 (FIG. 21) during an injection molding process, as discussed below.

FIG. 23 is another isometric side view of the jaw 2104 of FIG. 21. As illustrated, the jaw 2104 further includes a contact plate 2302. The contact plate 2302 provides a structural location where the supply conductor 2116 (FIG. 21) may be coupled to the jaw 2104 to convey electrical energy thereto. In some embodiments, the contact plate 2302 may define a central aperture 2304, a plurality of holes 2306, and a through hole 2308. The central aperture 2304 may be configured to co-axially align with the central aperture 2112 (FIG. 21) of the jaw holder 2106 to receive an axle (e.g., the first axle 804a of FIGS. 9 and 10A-10B) therethrough. The holes 2306 may prove advantageous in helping secure the jaw 2104 to the jaw holder 2106 (FIG. 21) during an injection molding process, as discussed below. The through hole 2308 may prove advantageous in helping couple the supply conductor 2116 to the contact plate 2302 and in helping lock the jaw 2104 to the jaw holder 2106, as discussed more below.

In some embodiments, the hook member 2202 and the contact plate 2302 may be made of electrically-conductive materials, such as a metal, and the isolator 2204 may be made of a non-conductive material, such as ceramic or a high strength, high temperature plastic. In other embodiments, the isolator 2204 may also be made of an electrically-conductive material, without departing from the scope of the disclosure.

The hook member 2202 and the contact plate 2302 may each be machined from a larger piece of material or may alternatively be manufactured, such as through metal injection molding (MIM), machining, laser cutting, forming (bending), stamping, 3D printing, or any combination thereof. The isolator 2204 may be machined or may be molded using ceramic injection molding (CIM).

To assemble the jaw 2104, the shank 2206 of the hook member 2202 is received into the central passageway 2208 and the hook member 2202 may then be coupled to the isolator 2204. In at least one embodiment, the isolator 2204 may be brazed to the hook member 2202 at a radial shoulder 2308 defined on the shank 2206. In such embodiments, this brazed joint may prove advantageous in providing a repeatable seal that prevents bioburden and improves cleanability and sterilization of the end effector 2102 (FIG. 21). In addition, the brazed joint may help stiffen the end effector 2102 as compared to conventional hook-type end effectors.

The contact plate 2302 may then be coupled to the hook member 2202. Consequently, electrical energy conveyed to the contact plate 2302 will be transmitted to the hook member 2202. In some embodiments, the planar surface 2210 at the end of the shank 2206 may be resistance or laser welded to the contact plate 2302. In other embodiments, however, the shank 2206 may be coupled to the contact plate 2302 at other locations or in other ways, such as by using one or more mechanical fasteners.

FIGS. 24A and 24B are front and back views, respectively, of the first portion 2118a of the jaw holder 2106 following a first assembly sequence, according to one or more embodiments. The first portion 2118a may be injection molded or otherwise formed or situated over a portion of the contact plate 2302.

In FIG. 24A, the first portion 2118a provides and otherwise defines a cable passage 2402 that communicates with the contact plate 2302. As discussed below, the electrical conductor 2114 (FIG. 21) may be routed through the cable passage 2402 to allow the supply conductor 2116 (FIG. 21) to electrically communicate with (i.e., transmit electrical energy to) the contact plate 2302. In some embodiments, one or more retention features 2404 may be provided in the cable passage 2402 to help capture the electrical conductor 2114, as discussed below. In other embodiments, however, the cable passage 2402 may be formed in the contact plate 2302, without departing from the scope of the disclosure.

In FIG. 24B, the first portion 2118a may further provide an access passage 2406 eccentric to the central aperture 2112. The access passage 2406 operates similar to the access passage 1806 of FIGS. 18B, 19, and 20B) and may be best understood with reference thereto. The access passage 2406 communicates with the through hole 2308 (FIG. 24A) defined in the contact plate 2302. The access passage 2406 and the through hole 2308 cooperatively facilitate access to the contact plate 2302, which may help in the process of coupling the supply conductor 2116 to the contact plate 2302, as described herein.

FIG. 25 depicts the electrical conductor 2114 received within the first portion 2118a of the jaw holder 2106. Following the first assembly sequence that produces the first portion 2118a, the electrical conductor 2114 may be coupled to and placed in electrical communication with the jaw 2104. More specifically, the electrical conductor 2114 may be routed through and received by the cable passage 2402. A portion of the insulation layer may be stripped from the electrical conductor 2114 to expose and end of the supply conductor 2116, and the exposed portion of the supply conductor 2116 may be positioned adjacent the contact plate 2302. The supply conductor 2116 may then be coupled to the contact plate 2302, such as through resistance welding, crimping, or soldering. The coaxially aligned through hole 2308 and access passage 2406 (FIG. 24B) allows a resistance welder access for electrodes to form an opposing contact weld.

The retention features 2404 may be similar to or the same as the retention features 1804 of FIGS. 18A and 19 and, therefore, may be configured to engage the outer insulative layer of the electrical conductor 2114 and thereby help retain the electrical conductor 2114 within the cable passage 2402. The retention features 2404 substantially prevent the electrical conductor 2114 from reversing back through the cable passage 2402, which may prove advantageous in providing strain relief on the electrical conductor 2114 by helping to mitigate strain over several cycles of using the end effector 2102 (FIG. 21). Moreover, the retention features 2404 may prove advantageous in helping prevent the electrical conductor 2114 from moving during a subsequent overmold shot used to form the second portion 2118*b* (FIGS. 26A and 26B).

FIGS. 26A and 26B are front and back views, respectively, of the end effector 2102 following an injection molding process that forms the second portion 2118*b* of the jaw holder 2106, according to one or more embodiments. The second portion 2118*b* may be formed over the first portion 2118*a* and the magnitude of the injection pressure may be managed to prevent excess flash. The injection molding process may alternately be referred to as an "overmold shot."

During the overmold shot, the material for the second portion 2118*b* (e.g., plastic) fills and encapsulates a cavity 2602 that contains the contact plate 2302 (FIGS. 23 and 25) and the exposed portion of the supply conductor 2116 (FIG. 25). Accordingly, the overmold shot electrically isolates and insulates the contact plate 2302 and the adjacent exposed supply conductor 2116. Moreover, as seen in FIG. 26B, the overmold shot may also fill in the access passage 2406. Furthermore, the material of the second portion 2118*b* (e.g., plastic) may also fill in the holes 2306 (FIG. 23) defined in the contact plate 2303 and may encapsulate the mold profile 2212 (FIG. 22) defined on the isolator 2204. In addition, the material for the second portion 2118*b* may also flow into a clearance gap or annulus defined between the inner diameter of the central passageway 2208 (FIG. 22) and the outer diameter of the shank 2206 (FIG. 22). As will be appreciated, filling in the cavity 2602, the access passage 2406, the holes 2306, the clearance gap, and overmolding the mold profile 2212 provides interlocking features that help lock the first and second portions 2118*a,b* together and prevent separation.

Accordingly, the overmold shot encapsulates and electrically isolates the supply conductor 2116 and the jaw 2104 from adjacent electrically-conductive parts of the end effector 2102 (FIG. 21). Consequently, the electrical energy supplied to the jaw 1604 may have a reduced risk of inadvertent tissue damage due to unintended current leakage Moreover, the two overmolding shots also help fill in cracks and crevices in the end effector 2102 that might present a bioburden risk.

FIG. 27 is an enlarged isometric view of another example end effector 2702 that may be used with the surgical tool 600 of FIG. 6, according to one or more embodiments. Accordingly, in some applications, the end effector 2702 of FIG. 27 may replace the end effector 604 of FIGS. 6 and 8-12. The end effector 2702 may be similar in some respects to the end effector 604 and therefore may be best understood with reference thereto, where like numerals will represent like component not described again.

Similar to the end effector 604 of FIGS. 6 and 8-12, the end effector 2702 includes the first and second jaws 610, 612 rotatably mounted to the distal clevis 802*a* at the first axle 804*a*. The end effector 2702 also includes the first and second jaw holders 902*a,b* that receive and seat the first and second jaws 610, 612, respectively, for corresponding movement (rotation) therewith. Unlike the end effector 604 of FIGS. 6 and 8-12, however, the first axle 804*a* comprises a headed axle pin, as discussed below.

FIG. 28 is a cross-sectional front view of the end effector 2702 of FIG. 27. As illustrated, first axle 804*a* has a first end 2802*a* and a second end 2802*b*, and an enlarged-diameter head 2804 is provided and otherwise defined at the first end 2802*a*. The head 2804 exhibits a first diameter 2806*a*, whereas the second end 2802*b* of the first axle 804*a* exhibits a second diameter 2806*b* that is smaller than the first diameter 2806*a*.

FIG. 28 also depicts how the first axle 804*a* may be mounted to the distal clevis 802*a*, which correspondingly mounts the jaws 610, 610 for rotation about the first axle 804*a*. The first arm 1004*a* defines a first aperture 2808*a* sized and otherwise configured to receive the first end 2802*a* and the head 2804, and the second arm 1004*b* defines a second aperture 2808*b* configured to receive and secure the second end 2802*b*. The first axle 804*a* may be secured to the distal clevis 802*a* at the second end 2802*b* via a variety of means, as discussed below. When securing the first axle 804*a* at the second end 2802*b*, the enlarged-diameter head 2804 is able to apply a compressive load (force) against the first and second jaw holders 902*a,b* at a radial shoulder 2810, which results in a zero tolerance stack without gaps between the jaw holders 902*a,b*, thus assuring point-to-point contact while opening and closing the jaws 610, 612.

FIG. 29 is an exploded view of the end effector 2702 of FIG. 27. To assemble the end effector 2702, the first and second jaw holders 902*a,b* may first be positioned in an opening 2902 defined between the opposing arms 1004*a,b* of the distal clevis 802*a*. The second end 2802*b* of the first axle 804*a* may then be progressively extended through the first aperture 2808*a* in the first arm 1004*a*, the central apertures 1102*a,b* of the jaw holders 902*a,b*, respectively, and lastly the second aperture 2808*b* in the second arm 1004*b*. The first end 2802*a* and the head 2804 may then be received in the first aperture 2808*a*.

To secure the first axle 804*a* to the distal clevis 802*a*, the second end 2802*b* may be coupled or attached to the distal clevis 802*a* at the second aperture 2808*b*. In some embodiments, the second end 2802*b* may be welded or brazed to the distal clevis 802*a* at the second aperture 2808*b*. In other embodiments, the second end 2802*b* may be threaded into the second aperture 2808*b*. In yet other embodiments, the second end 2802*b* may be secured to the second aperture 2808*b* end by orbital riveting the outer surface of the second end 2802*b*. In even further embodiments, the second end 2802*b* may be received within the second aperture 2808*b* via an interference or shrink fit.

While the second end 2802*b* is being attached to the distal clevis 802*a* at the second aperture 2808*b*, a compressive load (force) may be applied along the first axle 804*a* at the first end 2802*a*. The compressive load may force the radial shoulder 2810 of the enlarged-diameter head 2804 against the first and second jaw holders 902*a,b*, and thereby remove any gaps between the jaw holders 902*a,b* to provide a zero tolerance stack. This may prove advantageous in trapping the jaws 610, 612 within the assembly such that the jaws 610, 612 need not be welded to the respective jaw holders 902*a,b*. Consequently, the jaws 610, 612 may be made out of harder materials, such as 420 stainless steel or a ceramic, which do not exhibit good weld characteristics. Moreover, securing the first axle 804*a* to the distal clevis 802*a* while a compressive load (force) is applied ensures that opposing bearing surfaces 2904 of the jaws 610, 612 are maintained parallel to one another during operation. This may prove advantageous in assuring point-to-point contact while opening and closing the jaws 610, 612.

Embodiments disclosed herein include:

A. A surgical tool that includes a drive housing, an elongate shaft that extends from the drive housing, an end effector arranged at a distal end of the elongate shaft and having a jaw and a jaw holder that secures the jaw, a wrist that couples the end effector to the elongate shaft and includes a distal clevis having an axle that rotatably mounts the jaw holder to the distal clevis, and an electrical conductor that extends from the drive housing and supplies electrical energy to the jaw via a supply conductor, wherein at least one of the jaw holder and the axle is made of a non-conductive material that insulates the distal clevis from the electrical energy provided to the jaw.

B. An end effector that includes a distal clevis, an axle mounted to the distal clevis, a jaw holder rotatably mounted to the axle, a jaw secured to the jaw holder such that rotation of the jaw holder correspondingly rotates the jaw, and an electrical conductor that supplies electrical energy to the jaw via a supply conductor, wherein at least one of the jaw holder and the axle is made of a non-conductive material that insulates the distal clevis from the electrical energy provided to the jaw.

C. A method of operating a surgical tool that includes positioning the surgical tool adjacent a patient for operation, the surgical tool including a drive housing, an elongate shaft that extends from the drive housing, an end effector arranged at a distal end of the elongate shaft and having a jaw and a jaw holder that secures the jaw, a wrist that couples the end effector to the elongate shaft and includes a distal clevis having an axle that rotatably mounts the jaw holder to the distal clevis, wherein at least one of the jaw holder and the axle is made of a non-conductive material, and an electrical conductor that extends from the drive housing to the jaw. The method further including supplying electrical energy to the jaw via a supply conductor of the electrical conductor, and insulating the distal clevis from the electrical energy provided to the jaw with one or both of the jaw holder and the axle.

Each of embodiments A, B, and C may have one or more of the following additional elements in any combination: Element 1: wherein the end effector is configured for monopolar operation. Element 2: wherein the end effector is configured for bipolar operation. Element 3: wherein the non-conductive material is selected from the group consisting of a ceramic, a plastic, a thermoplastic or thermosetting polymer, a composite material, hard rubber, a metal with an insulative coating, and any combination thereof. Element 4: wherein the jaw is a first jaw, the jaw holder is a first jaw holder, and the end effector further comprises a second jaw and a second jaw holder that secures the second jaw, wherein the first and second jaw holders are rotatably mounted to the distal clevis at the axle, a first end cap that receives a first end of the axle and is secured within a first slot defined in the distal clevis, and a second end cap that receives a second end of the axle and is secured within a second slot defined in the distal clevis. Element 5: wherein the first jaw holder comprises a first portion that receives and secures the first jaw, and a second portion coupled to the first portion. Element 6: wherein the axle is made of the non-conductive material and defines a channel that receives the electrical conductor, and wherein the end effector further comprises a contact plate mounted to the axle adjacent the first and second jaws and in electrical communication with the supply conductor to transfer the electrical energy to the first and second jaws. Element 7: wherein the jaw provides a contact plate having the supply conductor coupled thereto and the jaw holder is made of at least one non-conductive material and comprises a first portion injection molded to the jaw and defining a cable passage through which the electrical conductor is extendable, and a second portion overmolded to the first portion to encapsulate and electrically insulate the contact plate and an exposed portion of the supply conductor. Element 8: further comprising one or more retention features defined in the cable passage to retain the electrical conductor within the cable passage.

Element 9: wherein the non-conductive material is selected from the group consisting of a ceramic, a plastic, a thermoplastic or thermosetting polymer, a composite material, hard rubber, a metal with an insulative coating, and any combination thereof. Element 10: wherein the jaw is a first jaw, the jaw holder is a first jaw holder, and the end effector further comprises a second jaw and a second jaw holder that secures the second jaw, wherein the first and second jaw holders are rotatably mounted to the distal clevis at the axle, a first end cap that receives a first end of the axle and is secured within a first slot defined in the distal clevis, and a second end cap that receives a second end of the axle and is secured within a second slot defined in the distal clevis. Element 11: wherein the supply conductor is secured to the first jaw at a pocket defined in the first jaw. Element 12: wherein the first jaw holder comprises a first portion that receives and secures the first jaw, and a second portion coupled to the first portion. Element 13: wherein the first portion is made of ceramic and the second portion is made of a plastic overmolded onto the first portion. Element 14: wherein the axle is made of the non-conductive material and defines a channel that receives the electrical conductor, and wherein the end effector further comprises a contact plate mounted to the axle adjacent the first and second jaws and in electrical communication with the supply conductor to transfer the electrical energy to the first and second jaws. Element 15: wherein the contact plate comprises an arcuate body having a contact surface positioned adjacent an arcuate bottom surface of each of the first and second jaws. Element 16: wherein the jaw provides a contact plate having the supply conductor coupled thereto and the jaw holder is made of at least one non-conductive material and comprises a first portion injection molded to the jaw and defining a cable passage through which the electrical conductor is extendable, and a second portion overmolded to the first portion to encapsulate and electrically insulate the contact plate and an exposed portion of the supply conductor. Element 17: further comprising one or more retention features defined in the cable passage to retain the electrical conductor within the cable passage. Element 18: wherein the jaw further comprises a hook member, a shank that extends from the hook member and is coupled to the contact plate, and an isolator that defines a central passageway to receive the shank, wherein the hook member and the contact plate are made of a conductive material, and the isolator is made of a non-conductive material.

By way of non-limiting example, exemplary combinations applicable to A, B, and C include: Element 4 with Element 5; Element 4 with Element 6; Element 7 with Element 8; Element 10 with Element 11; Element 10 with Element 12; Element 12 with Element 13; Element 10 with Element 14; and Element 14 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
   a drive housing;
   an elongate shaft that extends from the drive housing;
   an end effector arranged at a distal end of the elongate shaft and having a jaw and a jaw holder that receives and seats the jaw;
   a wrist that couples the end effector to the elongate shaft and includes a distal clevis and an axle extending through the jaw, the jaw holder, and the distal clevis to rotatably mount the jaw holder to the distal clevis, the distal clevis defining an open-ended slot extending to an outer periphery of the distal clevis in a direction perpendicular to a pivot axis of rotation of the axle;
   an end cap that receives an end of the axle and is secured within the open-ended slot;
   a pair of drive cables extending from the drive housing and terminating at the jaw holder; and
   an insulated electrical conductor separate from the pair of drive cables and extending from the drive housing and terminating at the jaw to supply electrical energy to the jaw,
   wherein the jaw holder and the axle are made of a non-conductive material that insulates the distal clevis from the electrical energy provided to the jaw.

2. The surgical tool of claim 1, wherein the end effector is configured for monopolar operation.

3. The surgical tool of claim 1, wherein the end effector is configured for bipolar operation.

4. The surgical tool of claim 1, wherein the non-conductive material is selected from the group consisting of a ceramic, a plastic, a thermoplastic or thermosetting polymer, a composite material, hard rubber, a metal with an insulative coating, and any combination thereof.

5. The surgical tool of claim 1, wherein the jaw is a first jaw, the jaw holder is a first jaw holder, and the open-ended slot is a first open-ended slot, the end cap is a first end cap, and the end of the axle is a first end of the axle, the end effector further comprises:
   a second jaw and a second jaw holder that receives and seats the second jaw, wherein the first and second jaw holders are rotatably mounted to the distal clevis at the axle; and
   a second end cap that receives a second end of the axle and is secured within a second open-ended slot defined in the distal clevis, the second open-ended slot extending in the direction perpendicular to the pivot axis of rotation of the axle.

6. The surgical tool of claim 5, wherein the first jaw holder comprises:
   a first portion that receives and secures the first jaw; and
   a second portion overmolded onto the first portion and defining a pulley that receives the pair of drive cables.

7. The surgical tool of claim 5, wherein the axles defines a channel that receives a channel that receives the insulated electrical conductor, and
   wherein the end effector further comprises a contact plate mounted to the axle adjacent the first and second jaws and in electrical communication with a supply conductor of the insulated electrical conductor to transfer the electrical energy to the first and second jaws.

8. The surgical tool of claim 1, wherein the jaw provides a contact plate having a supply conductor of the insulated electrical conductor coupled thereto and comprises:
   a first portion injection molded to the jaw and defining a cable passage through which the insulated electrical conductor is extendable; and
   a second portion overmolded to the first portion to encapsulate and electrically insulate the contact plate and an exposed portion of the supply conductor.

9. The surgical tool of claim 1, further comprising a pulley defined by the jaw holder and configured to receive and seat the pair of drive cables.

10. The surgical tool of claim 1, further comprising:
    a first recess defined in the jaw holder to receive and seat the jaw; and
    a spacer arranged laterally adjacent the jaw and received within a second recess defined in the jaw holder.

11. An end effector, comprising:
    a distal clevis;
    an end cap that receives an end of an axle and is secured to the distal clevis at an open-ended slot defined in the distal clevis, the open-ended slot extending to an outer periphery of the distal clevis in a direction perpendicular to a pivot axis of rotation of the axle;
    a jaw holder rotatably mounted to the axle;

a jaw secured to the jaw holder such that rotation of the jaw holder correspondingly rotates the jaw, wherein the axle extends through the jaw, the jaw holder, and the distal clevis; and an insulated electrical conductor terminating at the jaw to supply electrical energy to the jaw, wherein the jaw holder and the axle are made of a non-conductive material that insulates the distal clevis from the electrical energy provided to the jaw.

12. The end effector of claim 11, wherein the non-conductive material is selected from the group consisting of a ceramic, a plastic, a thermoplastic or thermosetting polymer, a composite material, hard rubber, a metal with an insulative coating, and any combination thereof.

13. The end effector of claim 11, wherein the jaw is a first jaw, the jaw holder is a first jaw holder, the end cap is a first end cap, the end of the axle is a first end of the axle, and the open-ended slot is a first open-ended slot, the end effector further comprises:
 a second jaw and a second jaw holder that secures the second jaw, wherein the first and second jaw holders are rotatably mounted to the distal clevis at the axle; and
 a second end cap that receives a second end of the axle and is secured within a second open-ended slot defined in the distal clevis, the second open-ended slot extending in the direction perpendicular to the pivot axis of rotation of the axle.

14. The end effector of claim 13, wherein a supply conductor of the insulated electrical conductor is secured to the first jaw at a pocket defined in the first jaw.

15. The end effector of claim 13, wherein the first jaw holder comprises:
 a first portion that receives and secures the first jaw; and
 a second portion overmolded onto the first portion.

16. The end effector of claim 15, wherein the first portion is made of ceramic and the second portion is made of a plastic overmolded onto the first portion.

17. The end effector of claim 13, wherein the axles defines a channel that receives the insulated electrical conductor, and
 wherein the end effector further comprises a contact plate mounted to the axle adjacent the first and second jaws and in electrical communication with a supply conductor of the insulated electrical conductor to transfer the electrical energy to the first and second jaws.

18. The end effector of claim 17, wherein the contact plate comprises an arcuate body having a contact surface positioned adjacent an arcuate bottom surface of each of the first and second jaws.

19. The end effector of claim 11, wherein the jaw provides a contact plate having a supply conductor of the insulated electrical conductor coupled thereto and comprises:
 a first portion injection molded to the jaw and defining a cable passage through which the insulated electrical conductor is extendable; and
 a second portion overmolded to the first portion to encapsulate and electrically insulate the contact plate and an exposed portion of the supply conductor.

20. The end effector of claim 11, further comprising:
 a first recess defined in the jaw holder to receive and seat the jaw; and
 a spacer arranged laterally adjacent the jaw and received within a second recess defined in the jaw holder.

21. A method of operating a surgical tool, comprising:
 positioning the surgical tool adjacent a patient for operation, the surgical tool including:
  a drive housing;
  an elongate shaft that extends from the drive housing;
  an end effector arranged at a distal end of the elongate shaft and having a jaw and a jaw holder that secures the jaw;
  a wrist that couples the end effector to the elongate shaft and includes a distal clevis having an axle that rotatably mounts the jaw holder to the distal clevis, the distal clevis defining an open-ended slot extending to an outer periphery of the distal clevis in a direction perpendicular to an axis of rotation of the axle, wherein an end cap that receives an end of the axle is secured at the open-ended slot; and
  an insulated electrical conductor extending from the drive housing to the jaw;
 supplying electrical energy to the jaw via the insulated electrical conductor; and
 insulating the distal clevis from the electrical energy provided to the jaw with one or both of the jaw holder and the axle, wherein at least one of the jaw holder and the axle is made of a non-conductive material.

* * * * *